United States Patent
Nikkhah et al.

(10) Patent No.: US 12,427,517 B2
(45) Date of Patent: Sep. 30, 2025

(54) MICROFLUIDIC DEVICES AND METHODS INCORPORATING ASSAY UNITS WITH MULTIPLE 3D SCAFFOLD REGIONS

(71) Applicants: Mehdi Nikkhah, Scottsdale, AZ (US); Ouse Sheblak, Scottsdale, AZ (US)

(72) Inventors: Mehdi Nikkhah, Scottsdale, AZ (US); Ouse Sheblak, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 739 days.

(21) Appl. No.: 17/725,076

(22) Filed: Apr. 20, 2022

(65) Prior Publication Data

US 2022/0339629 A1    Oct. 27, 2022

Related U.S. Application Data

(60) Provisional application No. 63/178,334, filed on Apr. 22, 2021.

(51) Int. Cl.
    *B01L 3/00*      (2006.01)
(52) U.S. Cl.
    CPC ... *B01L 3/502715* (2013.01); *B01L 2200/027* (2013.01); *B01L 2200/0647* (2013.01); *B01L 2300/0819* (2013.01)
(58) Field of Classification Search
    CPC ......... B01L 3/502715; B01L 2200/027; B01L 2200/0647; B01L 2300/0819;
    (Continued)

(56) References Cited

U.S. PATENT DOCUMENTS

| 7,371,400 | B2 * | 5/2008 | Borenstein | B29C 65/02 |
| | | | | 435/395 |
| 8,343,740 | B2 * | 1/2013 | Gonda | C12N 5/0671 |
| | | | | 435/284.1 |

(Continued)

OTHER PUBLICATIONS

Feng, J. et al., "An in situ Raman spectroscopy-based microfluidic "lab-on-a-chip" platform for non-destructive and continuous characterization of Pseudomonas aeruginosa biofilms," Chemical Communications, vol. 51, Apr. 2015, The Royal Society of Chemistry, pp. 8966-8969.

(Continued)

*Primary Examiner* — Brian J. Sines
(74) *Attorney, Agent, or Firm* — Withrow & Terranova, PLLC; Vincent K. Gustafson

(57) ABSTRACT

A microfluidic device includes multiple microfluidic assay units arranged on a substrate, with each assay unit including multiple scaffold regions each containing a three-dimensional scaffold with associated cells, and a media channel surrounding a fluid-permeable boundary portion of at least a second scaffold region, wherein a fluid-permeable interface between the media channel and the second scaffold region comprises a curved shape spanning an arc of more than 90 degrees. A third scaffold region may be provided. Boundaries between different scaffold regions, and between a scaffold region and the media channel, may include microposts that may be spaced apart in a curved configuration. A method for performing an assay utilizing such a device is further provided.

22 Claims, 14 Drawing Sheets

(58) Field of Classification Search
CPC ....... B01L 3/502707; B01L 2200/0668; B01L 2400/086; B01L 3/502761; C12M 23/16; C12M 25/14
See application file for complete search history.

(56) References Cited

U.S. PATENT DOCUMENTS

| | | | |
|---|---|---|---|
| 10,017,724 B2 | 7/2018 | Nikkhah et al. | |
| 10,712,339 B2 | 7/2020 | Nikkhah et al. | |
| 2012/0003732 A1* | 1/2012 | Hung | C12M 23/40 435/289.1 |
| 2013/0143230 A1* | 6/2013 | Tolias | C12Q 1/025 435/7.1 |
| 2016/0152945 A1* | 6/2016 | Blahut | C12M 23/24 435/297.1 |
| 2018/0105793 A1* | 4/2018 | Pathak | C12N 5/0075 |
| 2020/0326330 A1* | 10/2020 | Kundu | C12N 5/0062 |

OTHER PUBLICATIONS

Truong, D. et al., "Breast Cancer Cell Invasion into a Three Dimensional Tumor-Stroma Microenvironment," Scientific Reports, vol. 6, Article No. 34094, Sep. 2016, 18 pages.

Zhang, Z., et al., "An ROS-sensitive tegafur-PpIX-heterodimerloaded in situ injectable thermosensitive hydrogel for photodynamic therapy combined with chemotherapy to enhance the tegafur-based treatment of breast cancer," Biomaterials Science, vol. 9, Oct. 2020, Royal Society of Chemistry, 17 pages.

* cited by examiner

MICROFLUIDIC DEVICES AND METHODS INCORPORATING ASSAY UNITS WITH MULTIPLE 3D SCAFFOLD REGIONS

CROSS-REFERENCE TO RELATED APPLICATION(S)

This application claims priority to U.S. Provisional Patent Application No. 63/178,334 filed on Apr. 22, 2021, wherein the entire contents of the foregoing application are hereby incorporated by reference herein.

TECHNICAL FIELD

This disclosure relates to microfluidic devices, including devices incorporating multiple assay units that each include multiple cell-containing scaffold regions and associated methods of fabricating and using such devices.

BACKGROUND

Cancer, of all types, has become a leading cause of death around the world. Cancer therapies are extremely expensive, have a relatively low success rate, and frequently take a massive toll on the body of a cancer patient. Additionally, drug screening for cancer is not efficient as it is very time consuming, costly, is advantageously personalized to an specific patient, and typically requires large amounts of patient blood samples.

Cancer usually consists of tumor cells and the host stromal cells. Stromal cells have been previously studied and have been shown to have a major role in the tumor initiation, tumor progression, and eventual tumor metastasis. Tumor stroma mainly consists of basement membrane, stromal cells (e.g. fibroblast cells), extracellular matrix (ECM), immune cells, and vasculature. Within the tumor stroma, stromal cells are the most abundantly found component and are critical to all stages of cancer progression since they produce growth factors, chemokines, and ECM, all of which facilitates recruitment by a tumor of endothelial cell and pericytes. Metastatic dissemination of cancer cells is initiated by tumor angiogenesis and invasion of the cancer cells through their surrounding stroma toward blood vessels. It is extremely important to study interactions between the tumor cells and surrounding cells (e.g., stroma and vascular cells) in order to increase the understanding of how cancer develops and spreads, and how to develop more effective drugs and therapies to treat cancer and/or contain its spread.

Significant efforts have been undertaken in recent years toward studying the mechanism of cancer metastasis, using in vivo and in vitro models. Genetically modified animal models have been crucially important to define the molecular basis of disease progression, but using these models renders it difficult to independently study the effects of various microenvironmental cues (i.e., cell-cell communication, mechanical properties of the matrix) on cancer cells metastasis. Additionally, extensive testing of therapeutic compounds using in vivo models is costly.

As an alternative, in vitro assays have been widely used to study behavior (i.e., migration) of cancer cells. In vitro cell migration studies have conventionally been performed using two-dimensional (2D) rigid substrates, Boyden chambers, and transwell-based assays utilizing a simplified tumor microenvironment (TME) composed of tumor cells. While these platforms have permitted high-throughput analysis in an economical manner, they have not fully captured the complexities of a native three-dimensional (3D) tumor microenvironment, and have not provided the most physiologically relevant method for modeling TME and cell migration.

Recent advances in micro- and nanoscale (i.e. micropatterning, microfluidics) technologies have enabled the development of innovative platforms to study cancer cell migration within well-defined 3D microenvironments. Cells have been encapsulated in 3D hydrogel matrices to allow them to move freely in any direction, as well as increase their contact with their surroundings, making these models highly biomimetic. These models have been incorporated into microfluidic devices to provide a more lifelike in-vivo environment in comparison to relatively large-scale platforms such as petri dishes etc. However, most microfluidic tumor-on-a-chip devices have not included a stroma layer, which has limited the ability to study tumor-stroma interaction and tumor cell invasion.

Even after the development of microfluidic devices that incorporates both a tumor layer and a stroma layer (e.g., such as disclosed in U.S. Pat. Nos. 10,017,724 and 10,712,339, the efficiency of fabrication, surface treatment, and cell seeding processes have been limited.

Need exists in the art for physiologically relevant in vitro models that simulate tumor microenvironments, in order to study activity (including metastatic behavior) of cancer cells in response to various biophysical and biochemical stimuli, such as different conditions, pharmaceuticals, cell types, and so on.

SUMMARY

Disclosed herein is a microfluidic device that includes multiple microfluidic assay units arranged on a substrate, with each assay unit including multiple scaffold regions each containing a three-dimensional scaffold with associated cells, and a media channel surrounding a fluid-permeable boundary portion of at least a second scaffold region, wherein a fluid-permeable interface between the media channel and the second scaffold region comprises a curved shape spanning an arc of more than 90 degrees. Microposts may be arranged between respective scaffold regions. Each assay unit may be arranged within a circular footprint. Additionally disclosed is a method for performing an assay using a microfluidic device as described herein. Three-dimensional scaffolds are formed in respective scaffold regions of the assay units, and liquid media is supplied to the media channels thereof to permit fluid communication between contents of the media channel and at least the second scaffold region. Liquid media may be extracted from the media channel and analyzed. At least portions of the scaffolds may be digested, followed by removal of cells from the digested scaffolds, and analysis of these cells, wherein different scaffolds may be separately digested and their cellular contents separately analyzed.

In one aspect, the disclosure relates to a microfluidic device comprising: a substrate; and a plurality of microfluidic assay units arranged on the substrate, wherein each microfluidic assay unit of the plurality of microfluidic assay units comprises: a first scaffold region containing a first three-dimensional scaffold comprising one or more first cells; a second scaffold region containing a second three-dimensional scaffold comprising one or more second cells, wherein the second scaffold region surrounds, and is in contact with, a fluid-permeable boundary portion of the first scaffold region; and a media channel surrounding a fluid-permeable boundary portion of the second scaffold region, and permitting fluid communication between contents of the media channel and at least the second scaffold region, wherein a fluid-permeable interface between the media channel and the second scaffold region comprises a curved shape spanning an arc of more than 90 degrees.

In certain embodiments, each microfluidic assay unit further comprises: a first inlet port in fluid communication with the first scaffold region; a second inlet port and a second outlet port in fluid communication with the second scaffold region; and a media channel inlet port and a media channel outlet port in fluid communication with the media channel. Additionally, each microfluidic assay unit, including a respective first scaffold region, second scaffold region, media channel, first inlet port, second outlet port, media channel inlet port, and media channel outlet port, is arranged within a circular footprint.

In certain embodiments, microfluidic assay units of the plurality of microfluidic assay units are arranged on the substrate in a two-dimensional array, with the circular footprint of each microfluidic assay unit being spaced apart from the circular footprint of each other microfluidic assay unit of the plurality of microfluidic assay units In certain embodiments, for each microfluidic assay unit, the media channel comprises an inlet segment coupled with the media channel inlet port, an outlet segment coupled with the media channel outlet port, and a main segment arranged between the inlet segment and the outlet segment. Additionally, the main segment comprises a greater width than each of the inlet segment and the outlet segment.

In certain embodiments, the main segment contacts the fluid-permeable boundary portion of the second three-dimensional scaffold region.

In certain embodiments, for each microfluidic assay unit, the main segment comprises a substantially constant width and/or a semi-annular shape.

In certain embodiments, each microfluidic assay unit further comprises: a plurality of first microposts arranged between the first scaffold region and the second scaffold region; and a plurality of second microposts arranged at a boundary of the second scaffold region, and arranged between the second scaffold region and the media channel.

In certain embodiments, the first three-dimensional scaffold and the second three-dimensional scaffold each comprise a hydrogel.

In certain embodiments, for each microfluidic assay unit, the fluid-permeable interface between the media channel and the second scaffold region comprises a curved shape spanning an arc of at least 135 degrees, or at least 180 degrees.

In certain embodiments, for each microfluidic assay unit, the one or more first cells comprises at least one of migratory cells, stem cells, and tumor cells; and the one or more second cells comprises at least one of: adipocytes, fibroblasts, macrophages, T-cells, and monocytes.

In certain embodiments, each microfluidic assay unit further comprises a third scaffold region containing a third three-dimensional scaffold comprising one or more third cells, wherein the third scaffold region surrounds, and is in contact with, the fluid-permeable boundary portion of the second scaffold region; and for each microfluidic assay unit, the third scaffold region is arranged between the second scaffold region and the media channel, wherein the fluid-permeable interface between the media channel and the second scaffold region includes a portion of the third scaffold region.

In certain embodiments, the microfluidic device further comprises: a plurality of first microposts arranged between the first scaffold region and the second scaffold region; a plurality of second microposts arranged between the second scaffold region and the third scaffold region; and a plurality of third microposts arranged between the third scaffold region and the media channel.

In certain embodiments, for each microfluidic assay unit: the one or more first cells comprises at least one of migratory cells, stem cells, and tumor cells; the one or more second cells comprises at least one of adipocytes and fibroblasts; and the one or more third cells comprises at least one of macrophages, T-cells, monocytes, vascular cells, endothelial cells, smooth muscle cells, and pericytes.

In another aspect, the disclosure relates to a method for performing an assay utilizing a microfluidic device that comprises a substrate and a plurality of microfluidic assay units arranged on the substrate, wherein each microfluidic assay unit comprises (i) a first scaffold region, (ii) a second scaffold region containing a second three-dimensional scaffold comprising one or more second cells, wherein the second scaffold region surrounds, and is in contact with, a fluid-permeable boundary portion of the first scaffold region, and (iii) a media channel surrounding a fluid-permeable boundary portion of the second scaffold region, wherein a fluid-permeable interface between the media channel and the second scaffold region comprises a curved shape spanning an arc of more than 90 degrees, the method comprising: forming a first three-dimensional scaffold comprising a plurality of first cells in the first scaffold region; forming a second three-dimensional scaffold comprising a plurality of second cells in the second scaffold region; and supplying liquid media to the media channel to permit fluid communication between contents of the media channel and at least the second scaffold region.

In certain embodiments, the method further comprises, for each microfluidic assay unit, extracting liquid media from the media channel, and analyzing the extracted liquid media.

In certain embodiments, the method further comprises, for each microfluidic assay unit: digesting at least a portion of the first three-dimensional scaffold in the first scaffold region; removing at least some first cells of the plurality of first cells from the digested first three-dimensional scaffold of the first scaffold region; and analyzing the at least some first cells.

In certain embodiments, the method further comprises, for each microfluidic assay unit: digesting at least a portion of the second three-dimensional scaffold in the second scaffold region; removing at least some second cells of the plurality of second cells from the digested second three-dimensional scaffold of the second scaffold region; and analyzing the at least some second cells.

In certain embodiments, each microfluidic assay unit further comprises (iv) a third scaffold region that surrounds, and is in contact with, the fluid-permeable boundary portion of the second scaffold region, with the third scaffold region arranged between the second scaffold region and the media channel, and with the fluid-permeable interface between the media channel and the second scaffold region including a portion of the third scaffold region; the method further comprises forming a third three-dimensional scaffold comprising a plurality of third cells in the third scaffold region; and the supplying of liquid media to the media channel permits fluid communication between contents of the media channel and at least the second scaffold region through the third scaffold region.

In certain embodiments, the method further comprises, for each microfluidic assay unit: digesting at least a portion of the third three-dimensional scaffold in the third scaffold region; removing at least some third cells of the plurality of third cells from the digested third three-dimensional scaffold of the third scaffold region; and analyzing the at least some third cells.

In certain embodiments, the method further comprises performing imaging analysis of at least a portion of each microfluidic assay unit.

Additional aspects and embodiments will be apparent to one skilled in the art upon review of the specification and accompanying drawings.

DETAILED DESCRIPTION

Disclosed herein is a microfluidic device that includes multiple microfluidic assay units arranged on a substrate, with each assay unit including multiple scaffold regions each containing a three-dimensional scaffold with associated cells, and a media channel surrounding a fluid-permeable boundary portion of at least a second scaffold region, wherein a fluid-permeable interface between the media channel and the second scaffold region comprises a curved shape spanning an arc of more than 90 degrees. In certain embodiments, each microfluidic assay unit includes a third scaffold region that surrounds and is in contact with the fluid-permeable boundary portion of the second scaffold region, wherein the fluid-permeable interface between the media channel and the second scaffold region includes a portion of the third scaffold region. Boundaries between different scaffold regions, and between a scaffold region and the media channel, may include microposts that may be spaced apart in a curved configuration.

Figure 1:
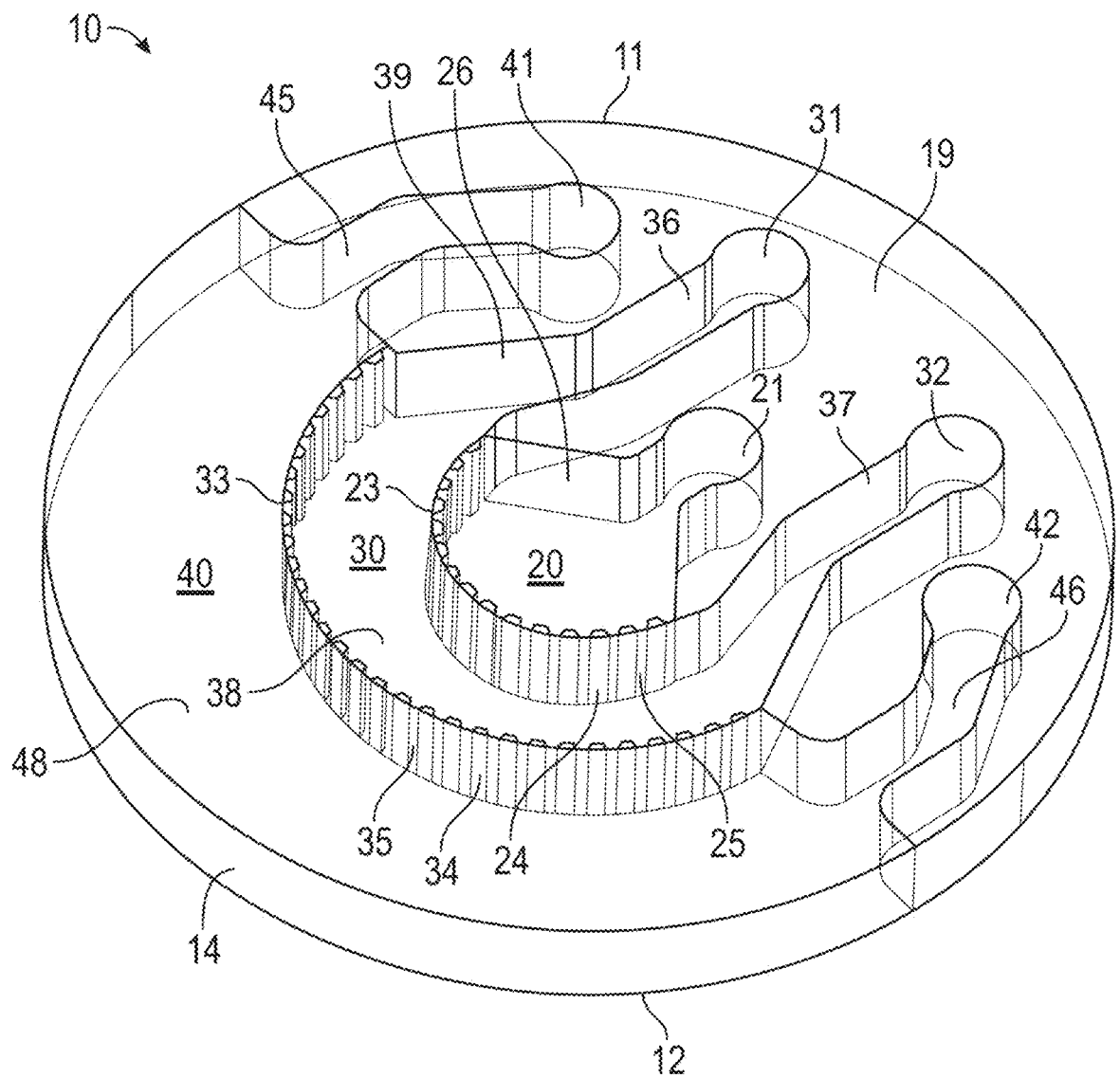
FIG. 1 is a perspective view of a single microfluidic assay unit of a microfluidic device according to one embodiment.

FIG. 1 is a perspective view of a single microfluidic assay unit 10 of a microfluidic device according to one embodiment. Although only a single microfluidic assay unit 10 is shown, it is to be appreciated that preferred microfluidic devices would include multiple microfluidic assay units 10 arranged in an array. As illustrated, the microfluidic assay unit 10 includes an upper surface 11 and an opposing lower surface 12 both bounded by a peripheral edge 14. The microfluidic assay unit further includes a first scaffold region 20 (at center), a second scaffold region 30 that surrounds a first fluid-permeable boundary portion 23 bounding a portion of the first scaffold region 20, and a media channel 40 that surrounds a second fluid-permeable boundary portion 33 bounding a portion of the second scaffold region 30. The second fluid-permeable boundary portion 33 between the media channel 40 and the second scaffold region 30 comprises a curved shape spanning an arc of about 180 degrees. As shown, the first scaffold region 20 is centrally arranged, and has a curved wedge-like shape with a first inlet port 21 that is offset relative to a vertex of the wedge-like shape. Approximately half of the first scaffold region 20 is bounded by a plurality of first microposts 24 arranged in a curved (e.g., approximately semi-circular) configuration and separated by gaps 25, providing a fluid-permeable boundary (i.e., the first fluid-permeable boundary portion 23) between the first scaffold region 20 and the second scaffold region 30. The first inlet port 21 permits fluid (e.g., precursor material, such as hydrogel precursor material, for forming a first scaffold to include one or more first cells) to be supplied to the first scaffold region 20, wherein angled walls 26 of the first scaffold region 20 cause a width of the first scaffold region 20 to expand gradually toward the curved first fluid-permeable boundary portion 23 defined by the plurality of first microposts 24. Such hydrogel precursor material (and one or more first cells therein) may be polymerized to form a first three-dimensional scaffold in the first scaffold region 20, with the plurality of first microposts 24 serving to contain the hydrogel precursor material and first three-dimensional scaffold in place while permitting fluid to through the gaps 25 between and past the first microposts 24.

With continued reference to FIG. 1, the second scaffold region 30 is arranged in a generally U-shaped configuration, with a second inlet port 31 and a second outlet port 32 at ends thereof. An inlet segment 36 and an outlet segment 37 extend from the respective second inlet and outlet ports 31, 32 to a truncated generally C-shaped portion 38 of the second scaffold region 30 that extends between (i) the first fluid-permeable boundary portion 23 defined by the plurality of first microposts 24 and (ii) the second fluid-permeable boundary portion 33 defined by the plurality of second microposts 34. Microposts of the plurality of second microposts 34 are spaced apart by gaps 35 along a curve having a semicircular shape and that spans an arc of about 180 degrees, to provide a fluid-permeable interface between the second scaffold region 30 and the media channel 40. The second inlet port 31 permits fluid (e.g., precursor material, such as hydrogel precursor material, for forming a second three-dimensional scaffold to include one or more second cells) to be supplied to the second scaffold region 30. Such hydrogel precursor material (and one or more second cells therein) may be polymerized to form a second three-dimensional scaffold in the second scaffold region 30, with the plurality of second microposts 34 serving to contain the hydrogel precursor material and second three-dimensional scaffold in place while permitting fluid to permeate between gaps 35 and past the second microposts 34. A solid boundary region 19 devoid of any channels, scaffolds, or other items is provide around the first port 21 outside the first scaffold region 20, around the second inlet and outlet ports 31, 32 outside the second scaffold region 30, and around the media channel inlet and outlet ports 41, 42 outside the media channel 40.

Presence of the first inlet port 21, the second inlet port 31, and the second outlet port 32 permits scaffold precursor material (e.g., hydrogel solution) supplied to the respective first scaffold region 20 and the scaffold region 30, and distributed therein. In certain embodiments, a suspension of first cells in a hydrogel solution may be supplied through the first inlet port 21 into the first scaffold region 20 to fill the first scaffold region 20 and contact the plurality of first microposts 24. Thereafter, the hydrogel solution may be polymerized within the cell suspension in the first scaffold region 20 to form a first three-dimensional scaffold (e.g., hydrogel matrix) having first cells embedded therein. Additionally, a suspension of second cells in a hydrogel solution may be supplied through the second inlet port 31 into the second scaffold region 30 to fill the second scaffold region 30 and contact the plurality of second microposts 34. Angled walls 39 provide an expanding channel width transition between the inlet segment 31 and the generally C-shaped portion 38 of the second scaffold region 30. After the hydrogel solution is supplied through the second inlet port 31, this hydrogel solution may be polymerized within the cell suspension in the second scaffold region 30 to form a second three-dimensional scaffold (e.g., hydrogel matrix) having second cells embedded therein. Such polymerization may be accomplished by at least one of thermal, chemical, or photonic polymerization. In certain embodiments, a hydrogel precursor solution may be cured by placing the microfluidic device 10 in an incubator (e.g., for 30 minutes or more at 37° C. in a 5% $CO_2$ atmosphere in certain embodiments).

FIG. 1 also shows a media channel 40 that is arranged in contact with, and surrounds, the second fluid-permeable boundary portion 33 defined by the plurality of second microposts 34. The media channel 40 includes a media channel inlet port 41, an inlet segment 45 coupled with the media channel inlet port 41, a media channel outlet port 42, an outlet segment 46 coupled with the media channel outlet port 42, and a main segment 48 extended between the inlet segment 45 and the outlet segment 46. Liquid media may be supplied to the media channel 40 after formation of the first three-dimensional scaffold (in the first scaffold region 20) and the second three-dimensional scaffold (in the second scaffold region 30). The main segment 48 is shaped in a roughly semi-annular shape and has a substantially constant width, with the main segment 48 having a significantly greater width (e.g., at least two times or at least three times greater width) than each of the inlet segment 45 and the outlet segment 46. Providing a narrower width inlet segment 45 has been observed to promote reduce bubble formation during loading of liquid media into the media channel 40, and to reduce the requisite media loading pressure to fill the media channel 40, thereby reducing the possibility of damaging a second three-dimensional scaffold in the second scaffold region 30 during a liquid media loading step. As shown in FIG. 1, the first scaffold region 20, second scaffold region 30, media channel 40, and all associated ports 21, 31, 32, 41, 42 fit within a circular footprint (bounded by peripheral edge 14). Additionally, the first scaffold region 20, second scaffold region 30, and media channel 40 may be substantially coplanar with one another, while being bounded laterally (around peripheral edge 14) and from above (along upper surface 11) by a material such as PDMS, and bounded from below (along lower surface 12) by a substrate (not shown) of a rigid material such as glass or the like.

In certain embodiments, first cells of a first three-dimensional scaffold (provided in the first scaffold region 20) may comprise at least one of migratory cells, stem cells, and tumor cells, while second cells of a second three-dimensional scaffold (provided in the second scaffold region 30) may comprise at least one of: adipocytes, fibroblasts, macrophages, T-cells, and monocytes.

Figure 2:
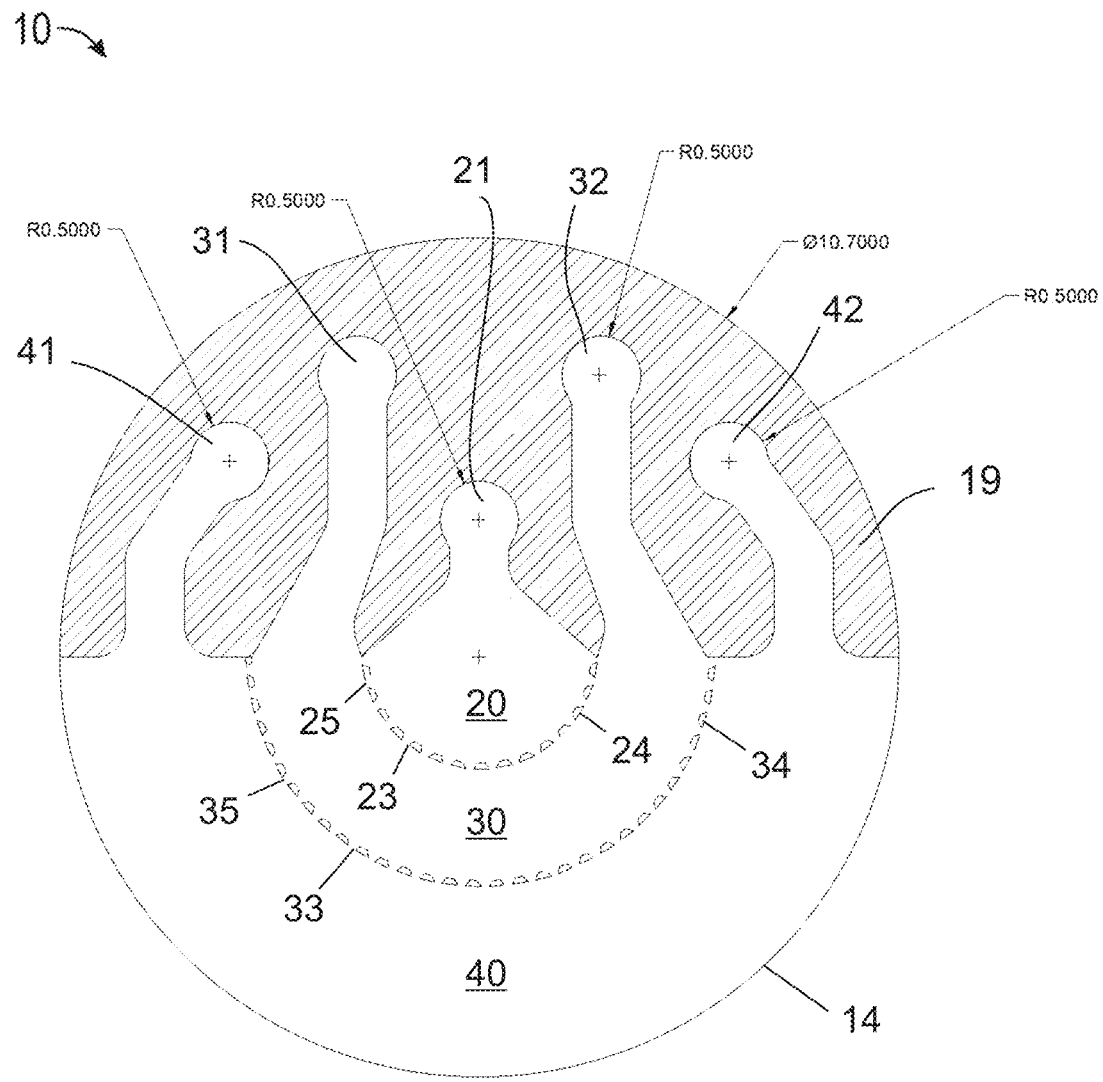
FIG. 2 is a top plan view illustration of the first scaffold region, second scaffold region, media channel, plurality of first microposts, plurality of second microposts, and media channel of the microfluidic array unit of FIG. 1.

FIG. 2 is a top plan view illustration of the microfluidic array unit 10 of FIG. 1, including the first scaffold region 20 (and first inlet port 21), the second scaffold region 30 (and second inlet and outlet ports 31, 32), the media channel 40 (and associated media channel inlet and outlet ports 41, 42), first liquid-permeable boundary portion 23 (including the plurality of first microposts 24 separated by first gaps 25), and the second liquid-permeable boundary portion 33 (including the plurality of second microposts 34 separated by first gaps 35). Each micropost of the pluralities of first and second micoposts 24, 34 may have a generally trapezoidal cross-sectional shape. In certain embodiments, each micropost of the pluralities of first and second micoposts 24, 34 may be spaced apart from at least one other adjacent micropost by the first and second gaps 25, 35, which may have widths in a range of from 50 to 300 microns (or in a subrange of from 75 to 200 microns, or from 75 to 150 microns, or from 80 to 125 microns, or about 100 microns. In certain embodiments, each micropost 24, 34 may have a length:width ratio in a range of from about 1.5:1 to about 10:1, or in a subrange of from about 1.5:1 to 5:1, or in a subrange of about 2:1 to 3:1, or about 2:1. In certain embodiments, a larger side of each trapezoidal micropost 24, 34 has a length of about 200 microns, and a shorter side of each trapezoidal micropost 24, 34 has a length of about 100 microns. As shown, each port 21, 31, 32, 41, 42 may have a radius of 0.5 mm, and the entire microfluidic array unit 10 may have a diameter (along peripheral edge 14) of 10.7 mm. A solid boundary region 19 devoid of any channels, scaffolds, or other items is provided around the first port 21 outside the first scaffold region 20, around the second inlet and outlet ports 31, 32 outside the second scaffold region 30, and around the media channel inlet and outlet ports 41, 42 outside the media channel 40.

In certain embodiments, a microfluidic device including multiple microfluidic assay units (e.g., each according to microfluidic assay unit 10 of FIGS. 1 and 2) may resembling a credit card device, with dimensions of about 85.6 mm long and 54 mm wide, and with a thickness of 0.76 mm. In certain embodiments, the microfluidic device may have a thickness of 0.25 mm, 0.35 mm, 0.45 mm, 0.55 mm, 0.65 mm, 0.75 mm, 0.85 mm, 0.95 mm, 1 mm, 2 mm, 3 mm, or any value between any combination of the foregoing values. In certain embodiments, a width of channels (or segments thereof) from inlet ports is 0.75 mm. In certain embodiments, a radius of the circular footprint of each microfluidic array unit is 5.35 mm, which is equivalent to that of a well in a standard 48 well-plate. It is to be appreciated that a microfluidic device may have any suitable dimensions for the end use application. In certain embodiments, scaffold regions 20, 30 and media channels 40 each have a height of approximately 200 μm.

Figure 3:
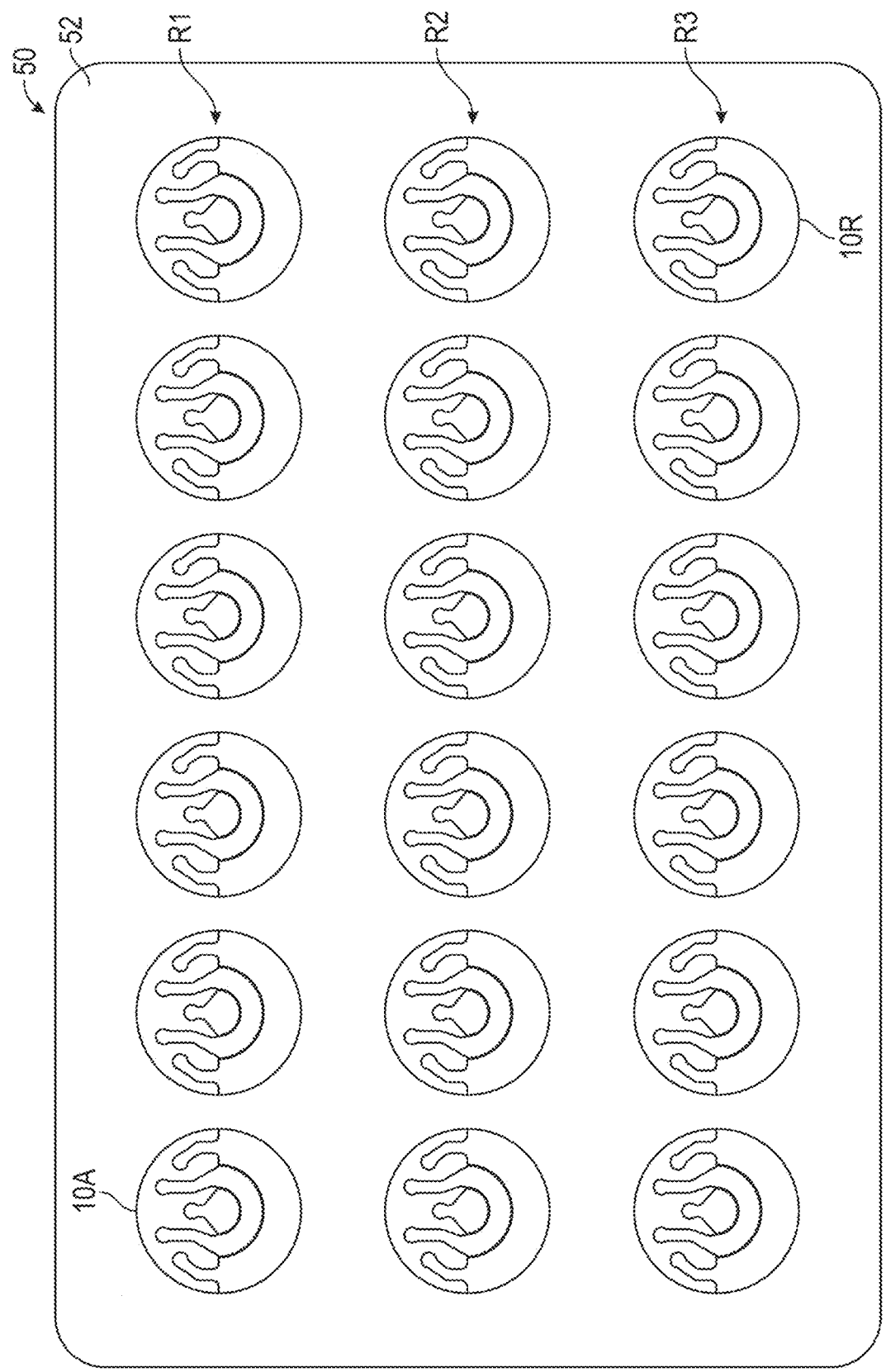
FIG. 3 is a top plan view of a microfluidic device including a substrate supporting eighteen (18) microfluidic assay units according to the design of FIGS. 1 and 2.
Figure 4:
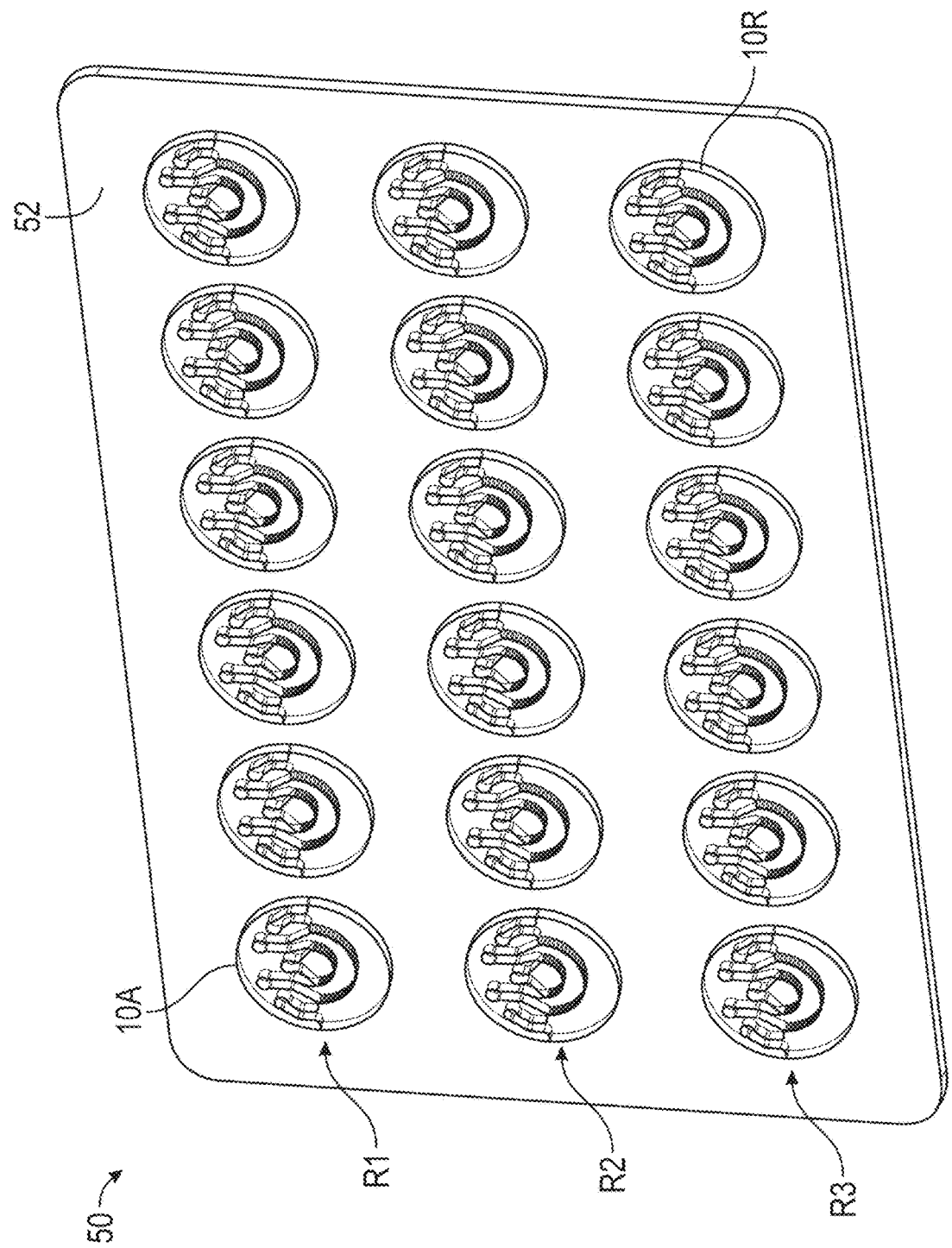
FIG. 4 is a perspective view of the microfluidic device of FIG. 3.

FIG. 3 is a top plan view, and FIG. 4 is a perspective view, of a microfluidic device 50 including a substrate 52 supporting eighteen (18) microfluidic assay units 10A-10R according to the design of FIGS. 1 and 2, with the microfluidic assay units arranged in an array of three rows R1-R2 each having six microfluidic assay units. The microfluidic device 50 may be of a size approximately equal to a credit card.

In certain embodiments, ports of a like type (e.g., all ports 21, all ports 31, all ports 32, all ports 41, all ports 42) among different microfluidic assay units (e.g., assay units 10A-10R of FIGS. 3 and 4) may be sized and spaced to receive fluid from a conventional multi-pipettor, thereby allowing fluid to be loaded into or removed from like regions of multiple microfluidic assay units (e.g., assay units 10A-10R) simultaneously.

In certain embodiments, microfluidic assay units may be arranged with spacing identical to wells of standard 48-unit well plate.

Figure 5:
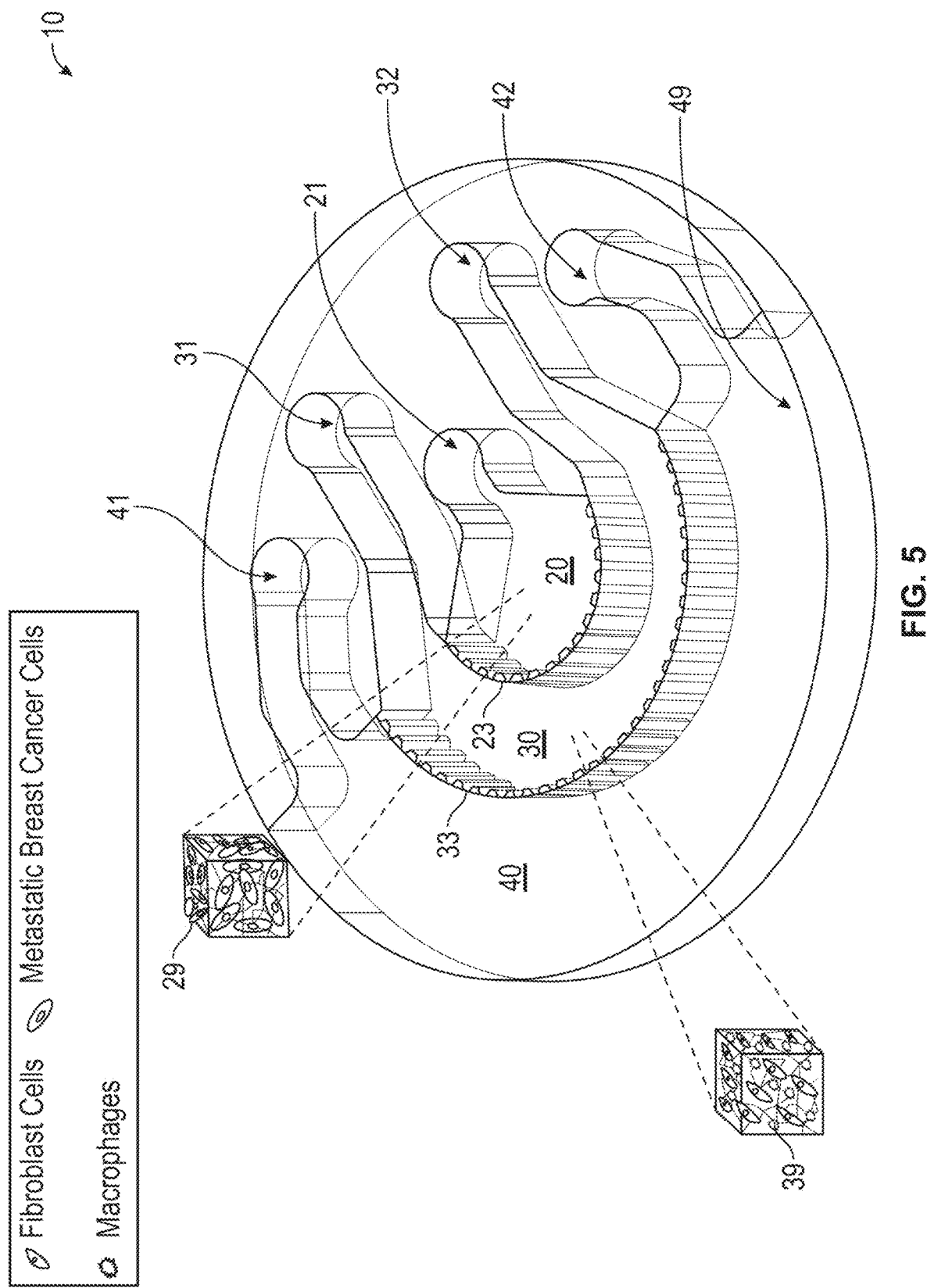
FIG. 5 is a perspective view illustration of a microfluidic assay unit according to the design of FIGS. 1 and 2.

FIG. 5 is a perspective view illustration of a microfluidic assay unit 10 according to the design of FIGS. 1 and 2, showing the placement of scaffolds 29, 39 within the first and second scaffold regions 20, 30, respectively. The first scaffold region 20 may serve as a tumor reservoir containing items such as a metastatic (e.g., breast or other tumor) cancer cells in a polymerized hydrogel scaffold 29 bounded by the first liquid-permeable boundary portion 23, and the second scaffold region 30 may serve as a stroma reservoir containing items such as fibroblast cells and microphages (eg., from a CAF co-culture) in a polymerized hydrogel scaffold 39 (bounded between the first liquid-permeable boundary portion 23 and the second liquid-permeable boundary portion 33). Examples of hydrogels that may be used to form the scaffolds 29, 39 include collagen type I hydrogel and/or fibrin hydrogel. The media channel 40 may contain cell culture media 49 and/or any other suitable fluid(s). The first inlet port 21 may be used to supply cancer cells and hydrogel to the first scaffold region 20. The second inlet port 31 may be used to supply stroma cells (e.g., fibroblast cells and macrophages) and hydrogel to the second scaffold region 30, and the second outlet port 32 may serve as a reservoir for the foregoing items (or vice-versa). The media inlet port 41 may be used to supply cell culture media to the media channel 40 and the media outlet port 42 may serve as a reservoir for the foregoing media (or vice-versa).

Figure 6:
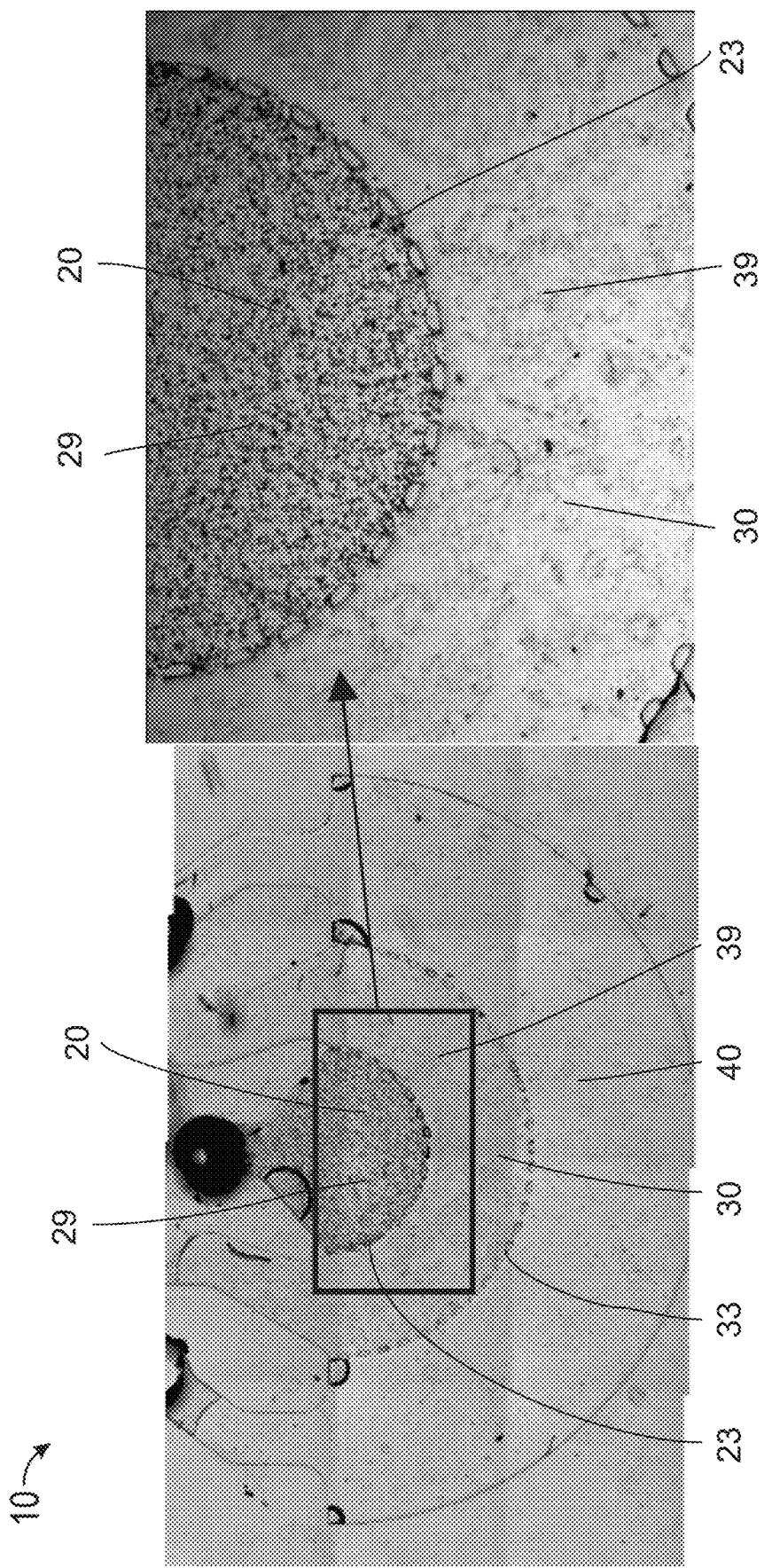
FIG. 6A is a photograph of a portion of a microfluidic assay unit fabricated on a substrate and in accordance with the design of FIGS. 1 and 2, with a first three-dimensional scaffold formed in the first scaffold region, and with a second three-dimensional scaffold formed in the second scaffold region.
FIG. 6B is a magnified portion of the photograph of the microfluidic assay unit shown in FIG. 6A.

FIG. 6A is a photograph of a portion of a microfluidic assay unit 10 fabricated on a substrate and in accordance with the design of FIGS. 1 and 2, with a first three-dimensional scaffold 29 formed in the first scaffold region 20, with a second three-dimensional scaffold 39 formed in the second scaffold region 30. The first and second scaffold regions 20, 30 are separated by the first liquid-permeable boundary portion 23, and the second scaffold region 30 is separated from the media channel 40 by the second liquid-permeable boundary portion 33. FIG. 6B is a magnified portion of the microfluidic assay unit of FIG. 6A, showing part of the first fluid-permeable boundary 23 with a plurality of first microposts distributed in an arc shape between the first scaffold region 20 (containing first scaffold 29) and second scaffold region (containing second scaffold 39).

Figure 7:
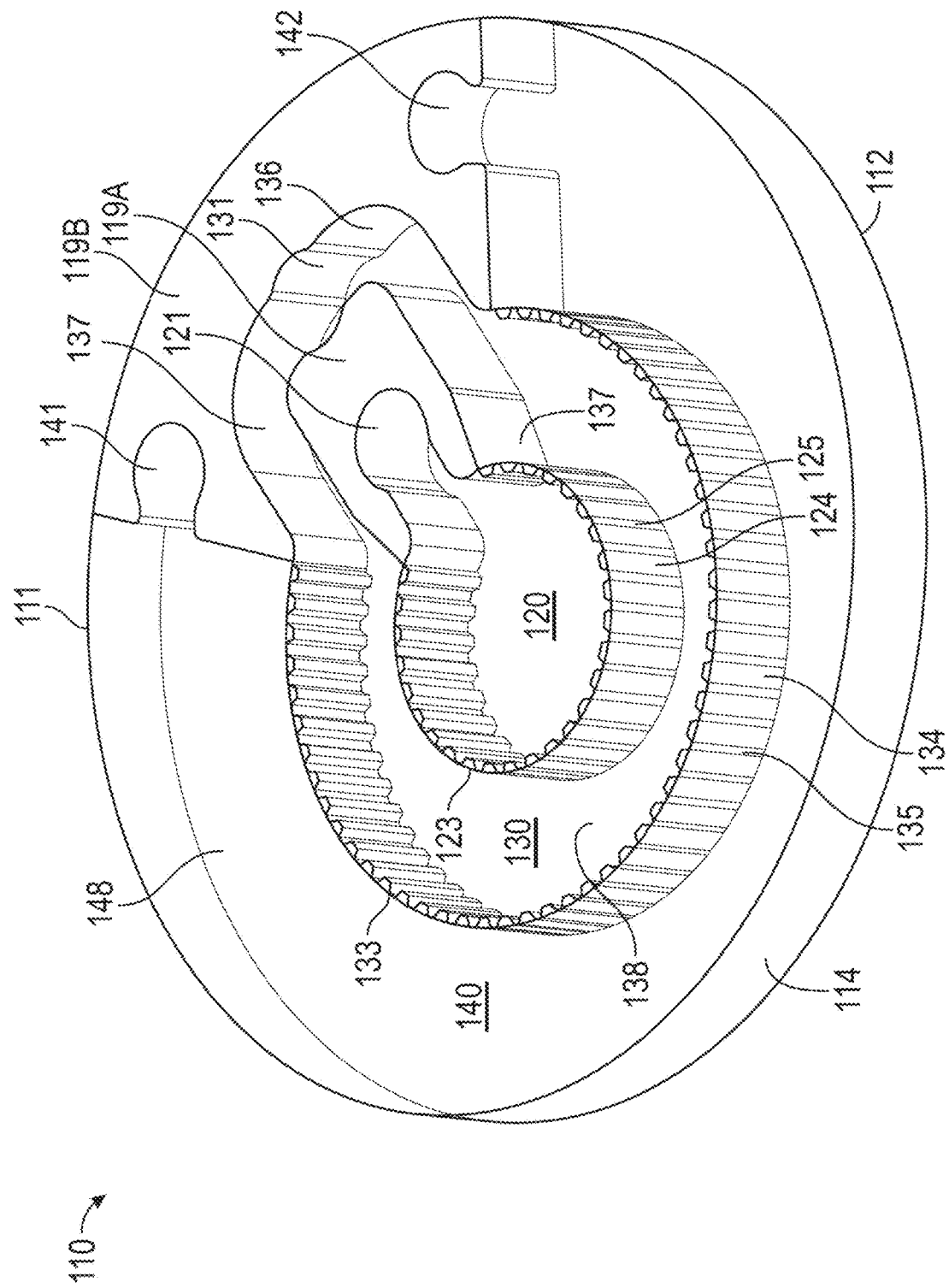
FIG. 7 is a perspective view of a perspective view of a single microfluidic assay unit of a microfluidic device according to one embodiment, with the embodiment including first and second scaffold regions and a media channel.

FIG. 7 is a perspective view of a single microfluidic assay unit 110 of a microfluidic device according to one embodiment, with the embodiment including a first scaffold region 120, a second scaffold region 130, and a media channel 140. Although only a single microfluidic assay unit 110 is shown, it is to be appreciated that preferred microfluidic devices would include multiple microfluidic assay units arranged in an array. As illustrated, the microfluidic assay unit 110 including a first scaffold region 120, a second scaffold region 130 that surrounds a first fluid-permeable boundary portion 123 bounding the first scaffold region 120, and a media channel 140 that surrounds a second fluid-permeable boundary portion 133 bounding the second scaffold region 130, with the foregoing items arranged between an upper surface 111 and an opposing lower surface 112 bounded by a peripheral edge 114. The first fluid-permeable boundary portion 123 includes a plurality of first microposts 124 (separated by first gaps 125) between the first and second scaffold regions 120, 130, and the second fluid-permeable boundary portion 133 includes a plurality of second microposts 134 (separated by first gaps 135) between the second scaffold region 130 and the media channel 140. The first scaffold region 120 is roughly circular in shape, with a first port 121 offset relative to the roughly circular remainder of the first scaffold region 120. The second scaffold region 130 forms a loop 137 with a single port 131 (instead of separate inlet and outlet ports) coupled thereto, with the loop 137 having a transverse segment 136 proximate to the single port 131. The media channel 140 extends from a media channel inlet port 141 to a media channel outlet port 142 around a curved path spanning about 220 degrees without any reduced width segments between the media channel ports 141, 142 and the wide media channel 140; additionally, the media channel 140 has a non-constant width that is reduced at a midpoint thereof. Solid boundary regions 119A-119B devoid of any channels, scaffolds, or other items are provide around the first port 121 outside the first scaffold region 120, around the second port 131, and around the media inlet and outlet ports 141, 142. The loop channel 137 configuration of the second scaffold region 130 of the microfluidic assay unit 110 of FIG. 7 has been observed to cause challenges in loading fluid material (e.g., hydrogel precursor material); in this regard, the microfluidic assay unit of FIG. 1 is currently believed to exhibit a preferred second scaffold region configuration.

Figure 8:
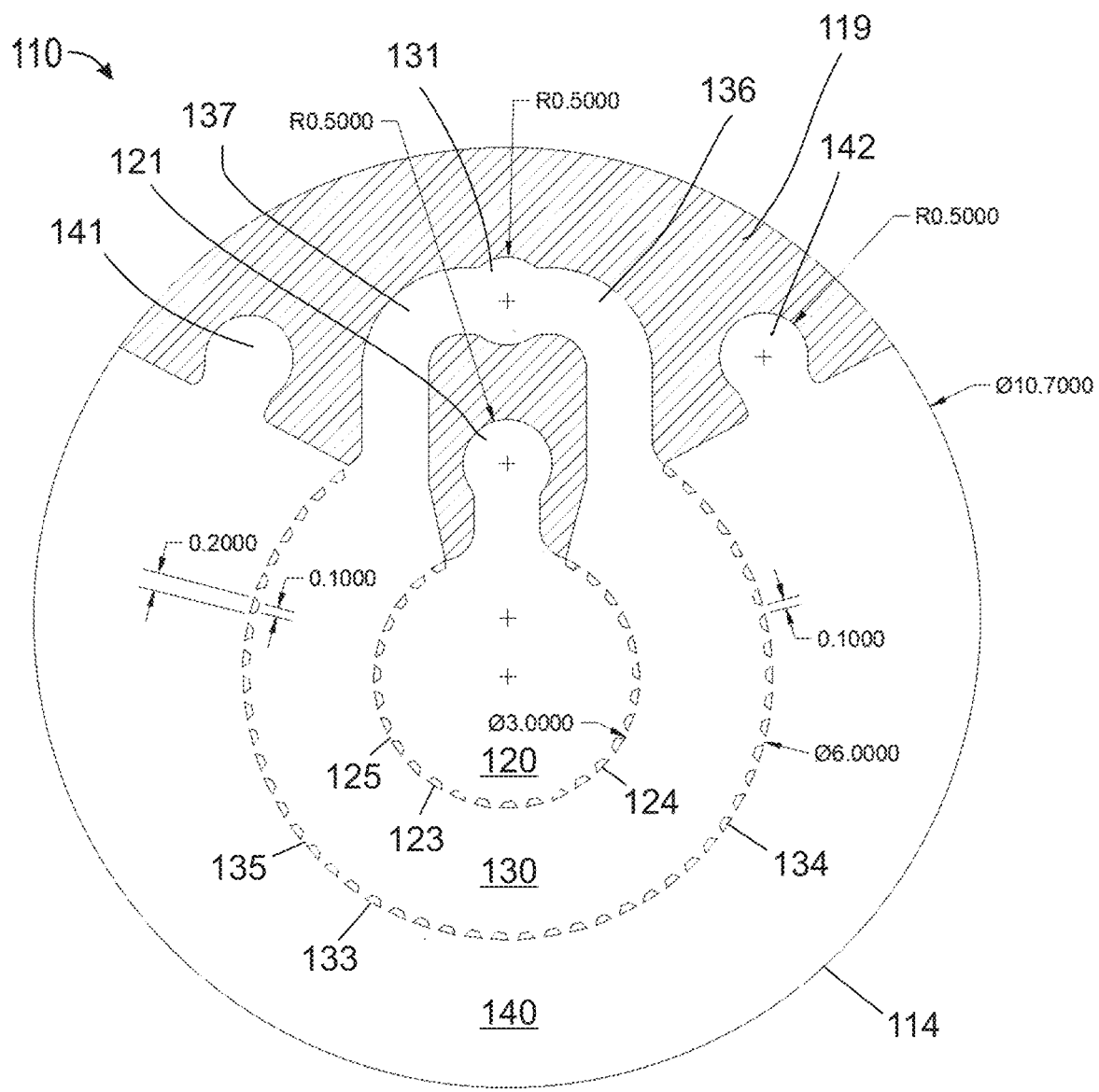
FIG. 8 is a top plan view illustration of the first scaffold region, second scaffold region, media channel, plurality of first microposts, plurality of second microposts, and media channel of the microfluidic array unit of FIG. 7.

FIG. 8 is a top plan view illustration of the microfluidic array unit of FIG. 7, including the first scaffold region 120, the second scaffold region 130, the media channel 140, the first liquid-permeable boundary region 123 (including the plurality of first microposts 124 separated by first gaps 125), and the second liquid-permeable boundary region 133 (including the plurality of second microposts 134 separated by second gaps 135). Each micropost 124, 134 may have a generally trapezoidal cross-sectional shape and dimensions as described previously herein, or as shown with a large (outer) side width of 0.2 mm and a shorter (inner) side width of 0.1 mm, with gaps 125, 135 between microposts of about 0.1 mm. As shown, each port 121, 131, 141, 142 may have a radius of 0.5 mm, and the entire microfluidic array unit 110 may have a diameter (along peripheral edge 114) of 10.7 mm. The first liquid-permeable boundary region 123 may have a diameter of 3 mm, and the second liquid-permeable boundary region 133 may have a diameter of 6 mm. Solid boundary regions 119A, 119B devoid of any channels, scaffolds, or other items are provided, including one solid boundary region 119A around the first port 121 outside the first scaffold region 120, and another solid boundary region 119B around the second port 131 outside the second scaffold region 130, and around the media channel inlet and outlet ports 141, 142 outside the media channel 140.

Figure 9:
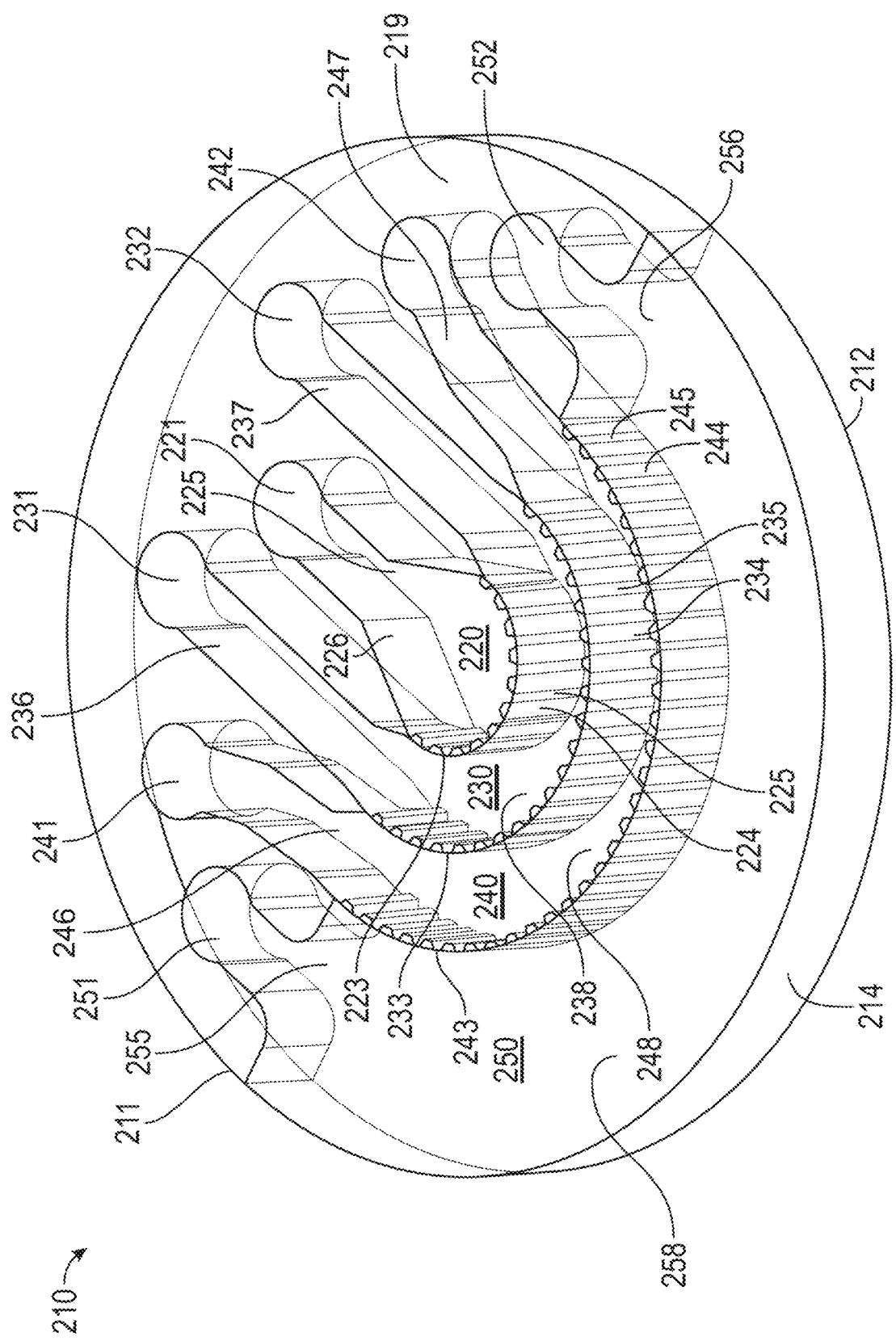
FIG. 9 is a perspective view of a perspective view of a single microfluidic assay unit of a microfluidic device according to one embodiment, with the embodiment including first through third scaffold regions and a media channel.

FIG. 9 is a perspective view of a single microfluidic assay unit 210 of a microfluidic device according to one embodiment, with the embodiment including first through third scaffold regions 220, 230, 240 and a media channel 250. Although only a single microfluidic assay unit 210 is shown, it is to be appreciated that preferred microfluidic devices would include multiple microfluidic assay units arranged in an array. As illustrated, the microfluidic assay unit 210 includes a first scaffold region 220 (at center), a second scaffold region 230 that surrounds a first fluid-permeable boundary portion 223 of the first scaffold region 220, a third scaffold region 240 that surrounds a second fluid-permeable boundary portion 233 of the second scaffold region 230, and a media channel 150 that surrounds the third fluid-permeable boundary portion 243 of the third scaffold region 240. A fluid-permeable interface between the media channel 250 and the third scaffold region 240 (including the third fluid-permeable boundary portion 243) comprises a curved shape spanning an arc of about 180 degrees. As shown, the first scaffold region 220 has a curved wedge-like shape with a first inlet port 221 that is offset relative to a vertex of the wedge-like shape. Approximately half of the first scaffold region 220 is bounded by the first fluid-permeable boundary portion 223 (including a plurality of first microposts 234 separated by first gaps 235) arranged in a curved (e.g., approximately semi-circular) configuration, providing a fluid-permeable boundary between the first scaffold region 220 and the second scaffold region 230. The first inlet port 221 permits fluid (e.g., precursor material, such as hydrogel precursor material, for forming a first scaffold to include one or more first cells) to be supplied to the first scaffold region 220, wherein angled walls 226 of the first scaffold region 220 cause a width of the first scaffold region 220 to expand gradually toward the curved first fluid-permeable boundary 223 defined by the plurality of first microposts 224.

With continued reference to FIG. 9, the second scaffold region 230 is arranged in a generally U-shaped configuration, with a second inlet port 231 and a second outlet port 232 at ends thereof. An inlet segment 236 and an outlet segment 237 extend from the respective second inlet port 231 and second outlet port 232 to a truncated generally C-shaped portion 238 of the second scaffold region 230 that extends between (i) the first fluid-permeable boundary 233 defined by the plurality of first microposts 234 and (ii) a second fluid-permeable boundary 243 defined by a plurality of second microposts 244. The plurality of second microposts 244 (separated by second gaps 245) are spaced apart along a curve having a semicircular shape and that spans an arc of about 180 degrees, to provide a fluid-permeable interface between the second scaffold region 230 and the third scaffold region 240. The second inlet port 231 permits fluid (e.g., precursor material, such as hydrogel precursor material, for forming a second three-dimensional scaffold to include one or more second cells) to be supplied to the second scaffold region 230.

FIG. 9 additionally illustrates a third scaffold region 240 having a generally C-shaped configuration, with a third inlet port 241 and third outlet port 242 at ends thereof. An inlet segment 246 and an outlet segment 247 extend from the respective third inlet port 241 and the third outlet port 242 to a truncated generally C-shaped portion 248 of the third scaffold region 240 that extends between (i) the second fluid-permeable boundary 233 defined by the plurality of second microposts 234 and (ii) third fluid-permeable boundary 243 defined by a plurality of third microposts 244 (separated by third gaps 245).

The media channel 250 of FIG. 9 comprises a generally semiannular shape, with inlet and outlet ports 251, 252 offset from ends thereof, and associated media inlet segment 255 and media outlet segment 256 arranged at either end of a main segment 258. The main segment 258 of the media channel 250 may have a substantially constant width extending around the plurality of third microposts 244. A solid boundary region 219 devoid of any channels, scaffolds, or other items is provide around the first port 221 outside the first scaffold region 220, around the second inlet and outlet ports 231, 232 outside the second scaffold region 230, around the third inlet and outlet ports 241, 241 outside the third scaffold region 240, and around the media channel inlet and outlet ports 251, 252 outside the media channel 250.

It is to be appreciated that the first scaffold region 220 may contain a first three-dimensional scaffold including one or more first cells, the second scaffold region 230 may contain a second three-dimensional scaffold including one or more second cells, and the third scaffold region 240 may contain a third three-dimensional scaffold including one or more third cells. In certain embodiments, the one or more first cells comprises at least one of migratory cells, stem cells, and tumor cells; the one or more second cells comprises at least one of adipocytes and fibroblasts; and the one or more third cells comprises at least one of macrophages, T-cells, monocytes, vascular cells, endothelial cells, smooth muscle cells, and pericytes.

Figure 10:
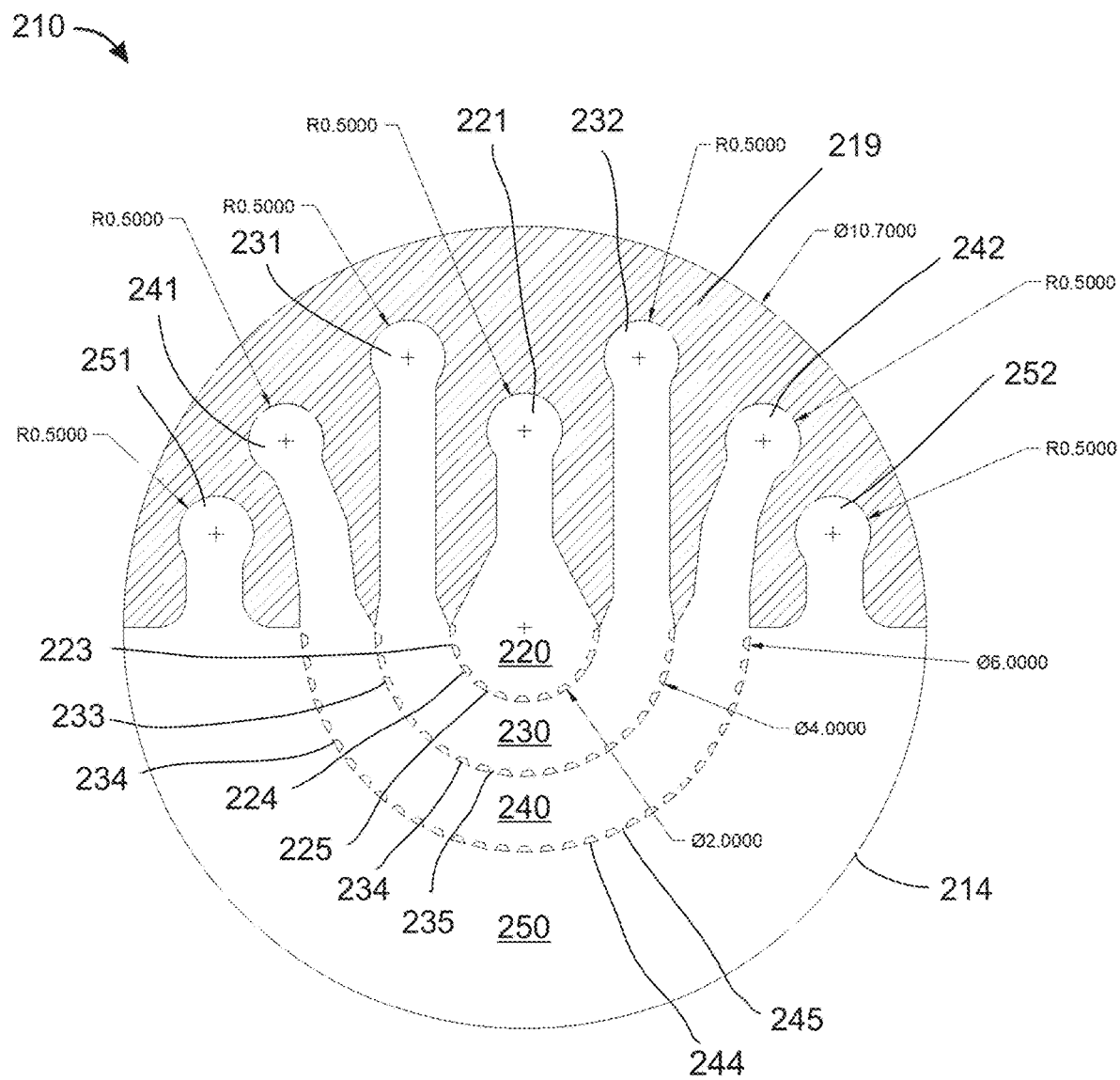
FIG. 10 is a top plan view illustration of the first to third scaffold regions, pluralities of first to third microposts, and media channel of FIG. 9.

FIG. 10 is a top plan view illustration of the microfluidic assay unit 210 of FIG. 9, including the first to third scaffold regions 220, 230, 240, the pluralities of first to third microposts 224, 234, 244, and media channel 250. Each micropost 224, 234, 244 may have a generally trapezoidal cross-sectional shape and dimensions as described previously herein. For a three-scaffold microfluidic assay unit according to FIG. 10, the footprint diameter is the same as described for the two-scaffold microfluidic array unit described previously in connection with FIGS. 1 and 2. For example, in certain embodiments, an array unit footprint diameter is 10.7 mm (around peripheral edge 214), the first scaffold region 220 has a 2 mm diameter, the second scaffold region 230 has a 4 mm diameter, and the third scaffold region 240 has a 6 mm diameter, with the respective regions being equally spaced. The various ports 221, 231, 232, 241, 242, 251, 252 may have diameters of 1 mm. Microposts 224, 234, 244 and gaps 225, 235, 245 may be of the same or substantially the same dimensions as those identified hereinabove (e.g., in connection with the two-scaffold microfluidic array unit of FIGS. 1 and 2).

Figure 11:
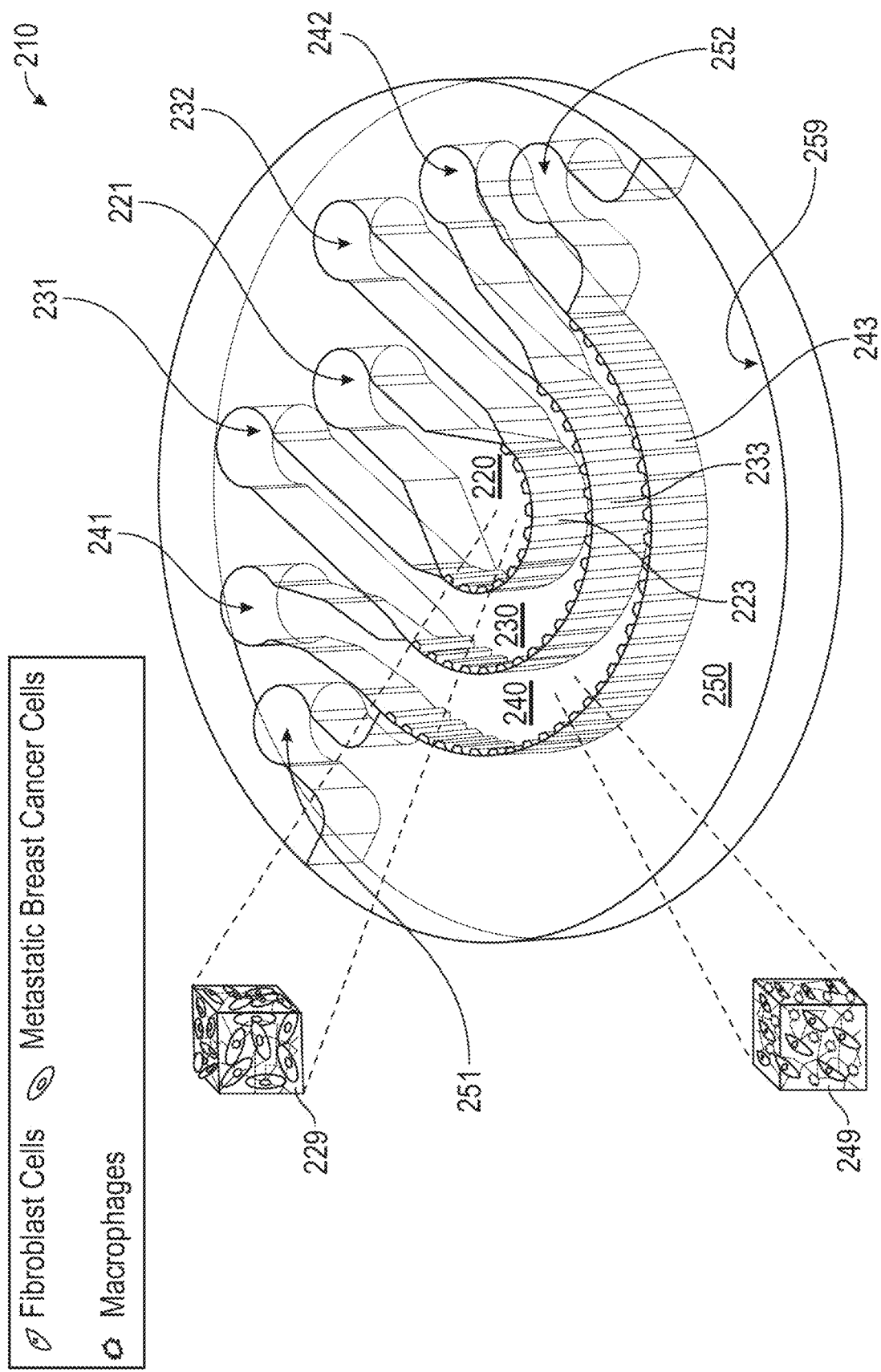
FIG. 11 is a perspective view illustration of a microfluidic assay unit according to the design of FIGS. 9 and 10.

FIG. 11 is a perspective view illustration of a microfluidic assay unit 210 according to the design of FIGS. 9 and 10, showing the placement of scaffolds 229, 249 in the first and third scaffold regions 220, 240, respectively. The first scaffold region 220 may serve as a tumor reservoir containing items such as a metastatic (e.g., breast or other tumor) cancer cells in a polymerized hydrogel scaffold 229 (supplied in liquid form between ports 221, 222), the second scaffold region 230 may include stroma containing items such as fibroblast cells and microphages (e.g., from a CAF co-culture) in hydrogel (supplied in liquid form between ports 231, 232), and the third scaffold region 240 may include vasculature cells/HUVEC material in hydrogel (supplied in liquid form between ports 241, 242). The first scaffold region 220 is bounded by the first liquid-permeable boundary portion 223, the second scaffold region 230 is bounded between the first and second liquid-permeable boundary portions 223, 233, and the third scaffold region 240 is bounded between the second and third liquid-permeable boundary portions 233, 243. Examples of hydrogels that may be used to form scaffolds include collagen type I hydrogel and/or fibrin hydrogel. The media channel 250 may contain cell culture media and/or any other suitable fluid(s), supplied between ports 251, 252.

Figure 12:
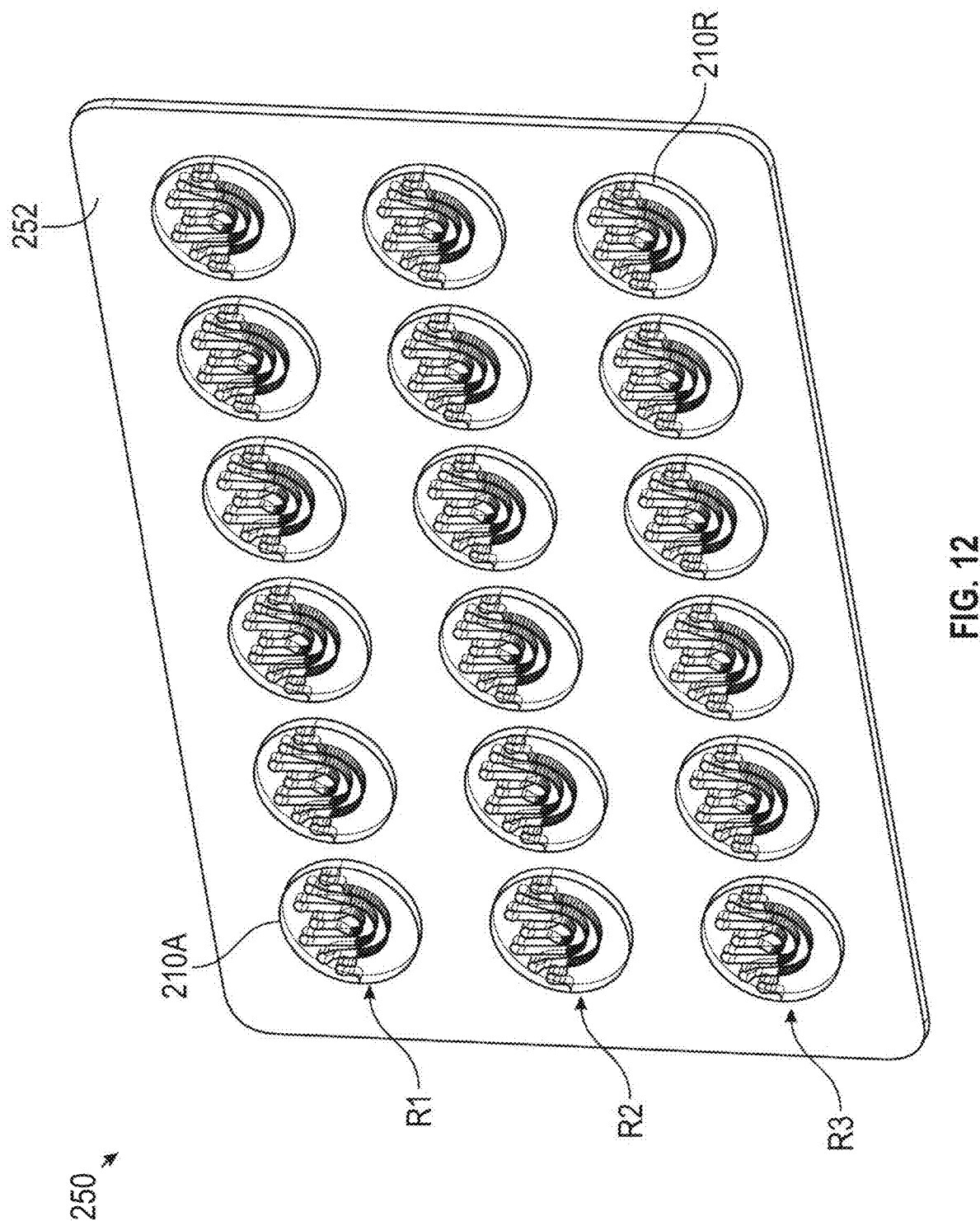
FIG. 12 is a perspective view of a microfluidic device including a substrate supporting eighteen (18) microfluidic assay units according to the design of FIGS. 9 and 10, with the microfluidic assay units arranged in an array of three rows of six microfluidic assay units.

FIG. 12 is a perspective view of a microfluidic device 250 including a substrate 252 supporting eighteen (18) microfluidic assay units 210A-210R according to the design of FIGS. 9 and 10, with the microfluidic assay units 210A-210R arranged in an array of three rows R1-R3 each including six microfluidic assay units. The microfluidic device 150 may be of a size approximately equal to a credit card. In certain embodiments, ports of a like type among different microfluidic assay units 210A-210R may be sized and spaced to receive fluid from a conventional multi-pipettor, thereby allowing fluid to be loaded into or removed from like regions of multiple microfluidic assay units 210A-210R simultaneously.

In one embodiments, photolithography and soft lithography were used to fabricate a microfluidic device that was designed using AutoCAD. To fabricate the master mold, a simple photolithography technique was used. An even layer of SU8-2075 (MicroChem) photoresist with a thickness of 200 µm was spun onto a silicon wafer. A transparent mask was placed above the wafer and the setup was exposed to UV light, forming the master mold. The master mold was taped onto a large petri dish for ease of use. To start the soft lithography for fabrication of the device, 30 g of polydimethylsiloxane (PDMS, Sylgard 184 Silicon Elastomer Kit, Dow Corning) was mixed in a plastic cup using the closed end of a transfer pipette with 3 g curing agent obtained from the same kit (10:1 ratio) and then placed into a desiccator for approximately 15 minutes to remove any formed bubbles. The PDMS was then casted onto the SU-8 wafer and baked for 90 minutes at 80° C. Afterwards, the PDMS was carefully peeled off and the inlets and outlets were then punched using a 1 mm biopsy punch. The open-channel side of the device was then bond to a glass slide using oxygen plasma treatment (PDC-32G, Harrick Plasma). The device was then sterilized by wet autoclave followed by a dry autoclave. The device the underwent surface treatment to make the channels and cell chambers hydrophobic, which started by injecting poly-d-lysine (PDL, Sigma Aldrich) of concentration of 1 mg/mL into the channels and the cell chambers. The device was then incubated at 37° C. for 1 hour, and then washed with deionized (DI) water. Afterwards, a 0.1% (v/v) glutaraldehyde ("GA", from Sigma Aldrich) solution was injected into the channels and cell chambers and incubated again at the same temperature for 1.5 hours. The device was then washed 4 times with DI water to make sure all the GA solution is removed, and then placed in an 80° C. oven overnight to render the device ready for use the next day.

Figure 13:
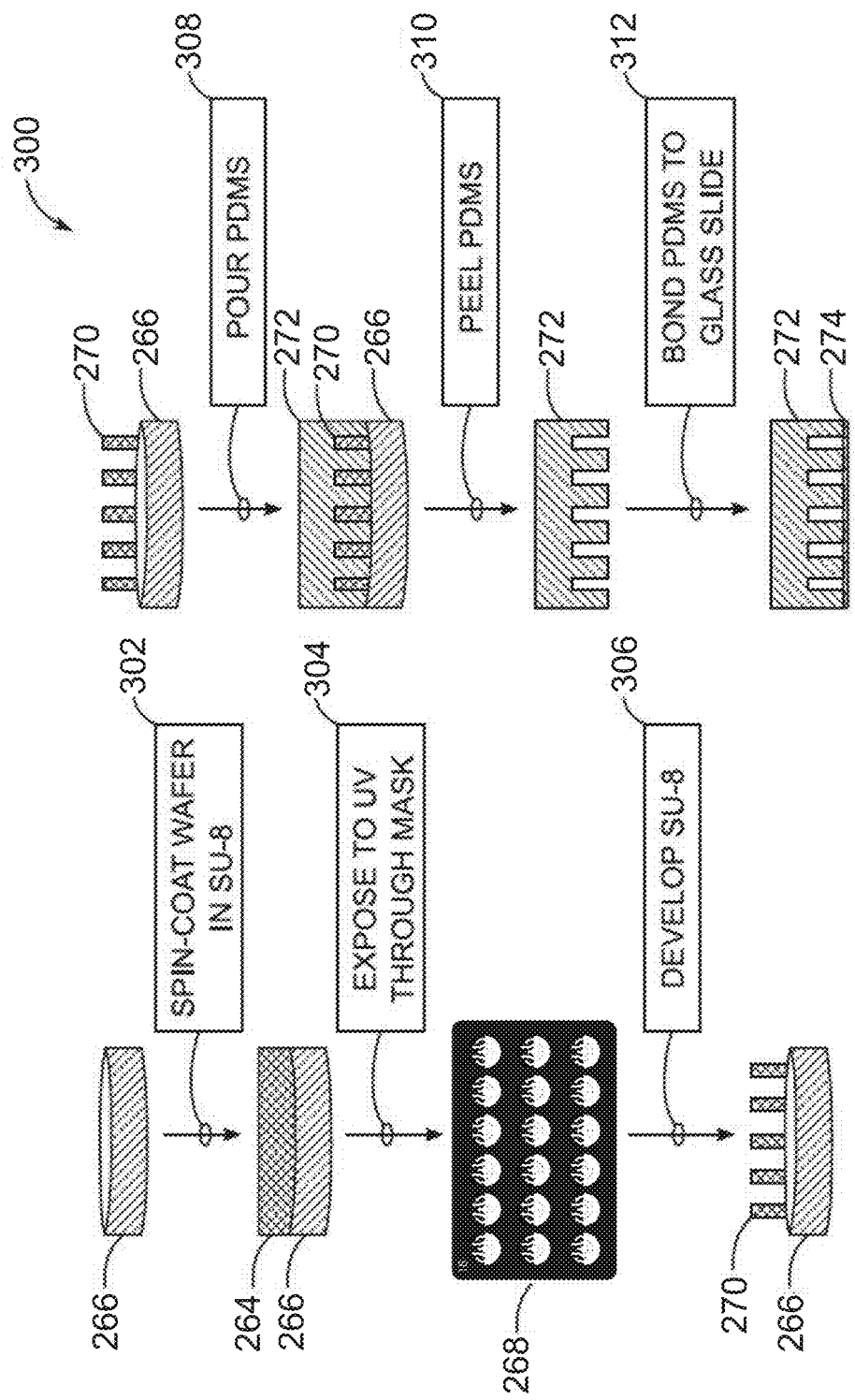
FIG. 13 is a schematic diagram showing steps of a method involving photolithography and replica molding for fabricating a microfluidic device as disclosed herein.

FIG. 13 is a schematic diagram showing steps of a method 400 involving photolithography and replica molding for fabricating a microfluidic device (e.g., devices 50, 250, etc. containing various assay units) as disclosed herein. Microfluidic devices as disclosed herein may be fabricated with PDMS using SU-8 photolithography and replica molding technique. The method starts at operation 302, with spin coating SU-8 photoresist 264 on a silicon wafer 266 to a thickness of 200 µm. Then, at operation 304 the coated wafer 266 is exposed to ultraviolet (UV) light through a transparent mask 268 with the microfluidic device design, created using AutoCAD (with minimum feature size of 20 µm). At operation 306, the SU-8 photoresist 264 is developed, resulting in a negative replica 270 of the microfluidic device. This negative replica 270 may be used to produce a positive replica 272 from the PDMS.

The wafer 266 is prepared for PDMS replica molding via silanization (e.g., using methyltrichlorosilane (MTCS)) of the surface to reduce attraction between the cast PDMS and the SU-8 features. The PDMS to be cast is prepared through mixing of the base to curing agent at a ratio of 10:1. At operation 308, this solution is poured over the silanized silicon wafer 266, then degassed in a vacuum and baked in an oven for 2 hours at 80° C. After polymerization, at operation 310 the PDMS is peeled from the wafer 266 and, in examples where an array of microfluidic devices (each including multiple microfluidic assay units as disclosed herein) are molded together, each microfluidic device in such an array may be cut. The inlet and outlet ports (i.e., openings to access scaffold regions and the media channel) may be cored downward through solid regions of the PDMS to the respective scaffold regions or media channels using standard punches (e.g., 1-2 mm diameter in some embodiments). At operation 312, the PDMS surfaces of the positive replica 272 are rendered hydrophilic through the use of air plasma, then bonded to glass slides 274 to create scaffold regions and media channels. The PDMS microfluidic platform is then sterilized at 120° C. for 20 minutes in a wet cycle, followed by a dry cycle at 120° C. for 35 minutes.

In certain embodiments, one or more electrodes may be provided on at least one surface of a substrate, and such electrode(s) may be in conductive electrical communication with an interior of the microfluidic device 10.

Figure 14A:
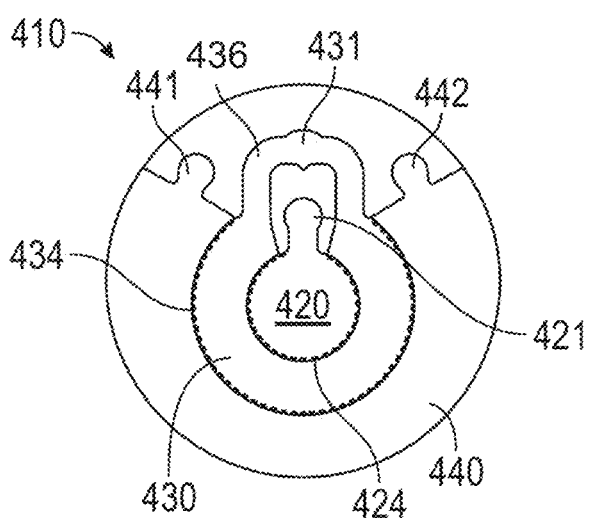
FIGS. 14A-14E illustrate microfluidic assay units according to five different designs, each having a circular footprint with a centrally arranged first scaffold region that is partially surrounded by a second scaffold region, with the second scaffold region being partially surrounded by a media channel.
Figure 14B:
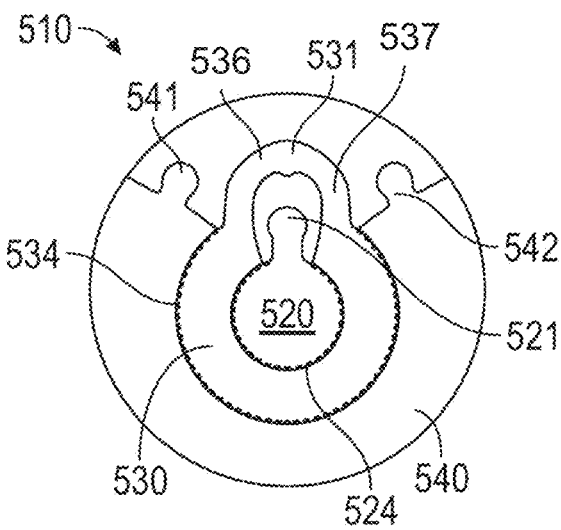

FIGS. 14A-14E illustrate microfluidic assay units 410, 510, 610, 10, 710, respectively according to five different designs, each having a circular footprint with a centrally arranged first scaffold region 420, 520, 620, 20, 720 that is partially surrounded by a second scaffold region 430, 530, 630, 30, 730, with the second scaffold region 430, 530, 630, 30, 730 being partially surrounded by a media channel 440, 540, 640, 40, 740. In each instance, a plurality of first microposts 424, 524, 624, 24, 724 is provided between the first scaffold region 420, 520, 620, 20, 720 and the second scaffold region 430, 530, 630, 30, 730, and a plurality of second microposts 434, 534, 634, 34, 734 is provided between the second scaffold region 430, 530, 630, 30, 730 and the media channel 440, 540, 640, 40, 740. In FIG. 14A, the first scaffold region 420 is roughly circular in shape, with a first port offset 421 relative to the roughly circular remainder of the first scaffold region 20. The second scaffold region 430 of FIG. 14A forms a loop 436 with a single port 432 (instead of separate inlet and outlet ports) coupled thereto, with the loop 436 having a transverse segment proximate to the single port 432. The media channel 440 of FIG. 14A extends from a media channel inlet port 441 to a media channel outlet port 442 around a curved path spanning about 220 degrees without any reduced width segments between the media channel ports 441, 442 and the wide media channel 440; additionally, the media channel 440 has a non-constant width that is reduced at a midpoint thereof. FIG. 14B illustrates a microfluidic assay unit 510 substantially similar to the one illustrated in FIG. 14A, but with the loop 536 of the second scaffold region 530 having a curved segment 537 proximate to the single second inlet port 531 associated with the second scaffold region 530. The first scaffold region 520 has an associated inlet port 521, and the media channel 540 has associated media channel inlet and outlet ports 541, 542.

Figure 14C:
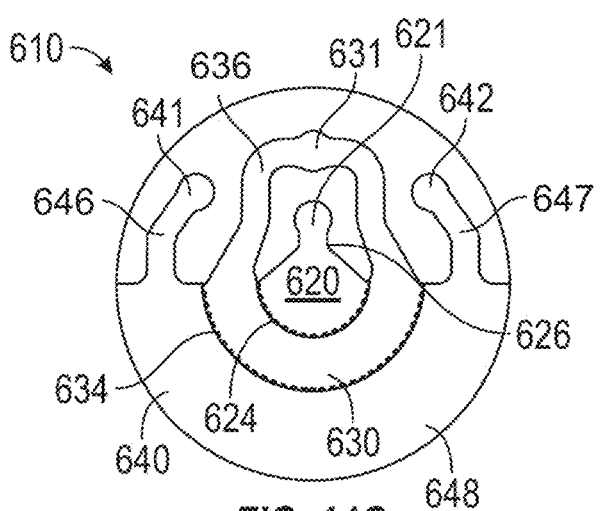

FIG. 14C illustrates a microfluidic assay unit 610 having a first scaffold region 620 having a curved wedge-like shape, with an inlet port 621 offset relative to an angled vertex portion 626 of the wedge-like shape. The second scaffold region 630 of FIG. 14C forms a loop 636 with a single port 631 (instead of separate inlet and outlet ports) coupled thereto, with the loop 636 having a transverse segment proximate to the single port 631. The media channel of FIG. 14C includes a media channel inlet port 641, an inlet segment 646 coupled with the media channel inlet port 641, a media channel outlet port 642, an outlet segment 647 coupled with the media channel outlet port 642, and a main segment 648 extending between the inlet segment 646 and the outlet segment 647. The main segment 648 is shaped in a roughly semi-annular shape spanning an arc length of about 180 degrees and has a substantially constant width, with the main segment 648 having a significantly greater width (e.g., at least two times or at least three times greater in width) than each of the inlet segment 646 and the outlet segment 647.

Figure 14D:
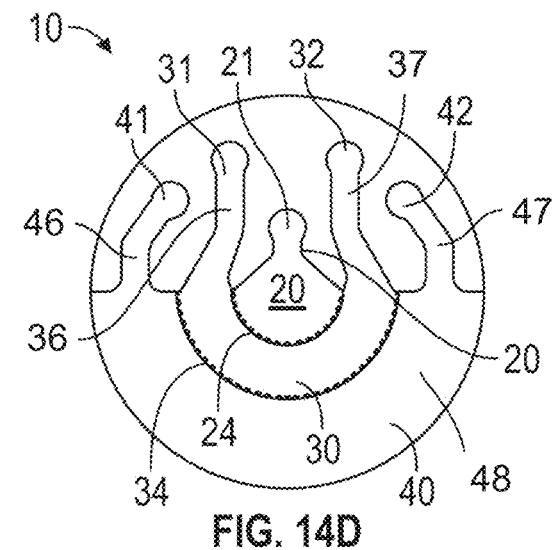

FIG. 14D illustrates a microfluidic assay unit 10 corresponding to the one shown in FIGS. 1 and 2. In comparison to the microfluidic assay unit 640 shown in FIG. 14C, the microfluidic assay unit 10 of FIG. 14D has a second scaffold region 30 arranged in a generally U-shaped configuration, with a second inlet port 31 and a second outlet port 32 at ends thereof. An inlet segment 36 and an outlet segment 37 extend from the respective second inlet port 31 and second outlet port 32 to a truncated generally C-shaped portion of the second scaffold region 30 that extends between (i) a first fluid-permeable boundary defined by a plurality of first microposts 24 and (ii) a second fluid-permeable boundary defined by a plurality of second microposts 34. The first scaffold region 20 and media channel 40 of FIG. 14D are the same as their counterparts 620, 640 in FIG. 14C. The media channel 40 of FIG. 14D includes a media channel inlet port 41, an inlet segment 46 coupled with the media channel inlet port 41, a media channel outlet port 42, an outlet segment 47 coupled with the media channel outlet port 42, and a main segment 48 (shaped in a roughly semi-annular shape spanning an arc length of about 180 degrees and has a substantially constant width) extending between the inlet segment 46 and the outlet segment 47.

Figure 14E:
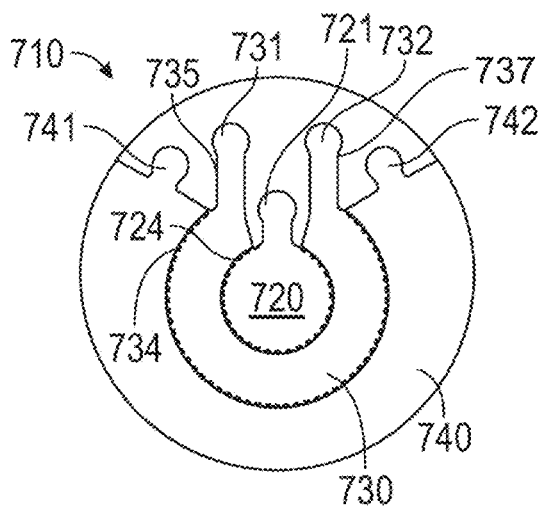

FIG. 14E illustrates a microfluidic assay unit 710 similar to the one shown in FIG. 14B, but with the second scaffold region 730 arranged in a generally U-shaped configuration, with a second inlet port 731 and a second outlet port 732 at ends thereof. An inlet segment 736 and an outlet segment 737 extend from the respective second inlet port 731 and outlet port 732 to a truncated generally C-shaped portion of the second scaffold region 730 that extends between (i) a first fluid-permeable boundary defined by a plurality of first microposts 724 and (ii) a second fluid-permeable boundary defined by a plurality of second microposts 734. The first scaffold region 720 and media channel 740 (with inlet and outlet ports 741, 742) of FIG. 14E are the same as their counterparts 540, 541, 542 in FIG. 14B.

Although various examples herein are directed to analysis of cancer cells, it is to be appreciated that the disclosure is not so limited, and that any suitable types of cells may be provided and analyzed using a microfluidic device 10 as disclosed herein.

As noted previously, the disclosure relates to a method for performing an assay utilizing a microfluidic device as disclosed herein. the method comprising: forming a first three-dimensional scaffold comprising a plurality of first cells in a first scaffold region; forming a second three-dimensional scaffold comprising a plurality of second cells in a second scaffold region; and supplying liquid media to the media channel to permit fluid communication between contents of the media channel and at least the second scaffold region. In certain embodiments, liquid media may be static after being supplied to the media channel. In certain embodiments, liquid media may be periodically or continuously flowed through a media channel.

In certain embodiments, the method further comprises, for each microfluidic assay unit, extracting liquid media from the media channel, and analyzing the extracted liquid media. Such extraction may be performed by aspiration with one or more pipettors. Analyses that may be performed on extracted media include, but are not limited to, proteomic analysis, ELISA, and exosome analysis.

In certain embodiments, the method further comprises, for each microfluidic assay unit: digesting at least a portion of the first three-dimensional scaffold (e.g., enzymatically digesting a hydrogel matrix with collagenase enzyme) in the first scaffold region; and removing at least some first cells of the plurality of first cells from the digested first three-dimensional scaffold of the first scaffold region; and analyzing the at least some first cells. The analysis may include gene expression analysis on extracted cells. These digestion, removal, and analysis may also be performed separately for second and third scaffold regions.

In certain embodiments, the method further comprises performing imaging analysis of at least a portion of each microfluidic assay unit. Examples of suitable imaging techniques that may be used include 3D confocal and fluorescence imaging, regular light microscopy, phase contrast microscopy. Imaging may be useful to permit analysis of protein expression, cell shape, cell morphology, and/or cell migration (e.g., speed and/or directionality).

Those skilled in the art will recognize improvements and modifications to the preferred embodiments of the present disclosure. All such improvements and modifications are considered within the scope of the concepts disclosed herein and the claims that follow

What is claimed is:

1. A microfluidic device comprising:
    a substrate; and
    a plurality of microfluidic assay units arranged on the substrate, wherein each microfluidic assay unit of the plurality of microfluidic assay units comprises:
    a first scaffold region containing a first three-dimensional scaffold comprising one or more first cells;
    a second scaffold region containing a second three-dimensional scaffold comprising one or more second cells, wherein the second scaffold region surrounds, and is in contact with, a fluid-permeable boundary portion of the first scaffold region; and
    a media channel surrounding a fluid-permeable boundary portion of the second scaffold region, and permitting fluid communication between contents of the media channel and at least the second scaffold region, wherein a fluid-permeable interface between the media channel and the second scaffold region comprises a curved shape spanning an arc of more than 90 degrees.

2. The microfluidic device of claim 1, wherein:
    each microfluidic assay unit further comprises:
    a first inlet port in fluid communication with the first scaffold region;

a second inlet port and a second outlet port in fluid communication with the second scaffold region; and
a media channel inlet port and a media channel outlet port in fluid communication with the media channel; and
each microfluidic assay unit, including a respective first scaffold region, second scaffold region, media channel, first inlet port, second outlet port, media channel inlet port, and media channel outlet port, is arranged within a circular footprint.

3. The microfluidic device of claim 2, wherein microfluidic assay units of the plurality of microfluidic assay units are arranged on the substrate in a two-dimensional array, with the circular footprint of each microfluidic assay unit being spaced apart from the circular footprint of each other microfluidic assay unit of the plurality of microfluidic assay units.

4. The microfluidic device of claim 1, wherein:
for each microfluidic assay unit, the media channel comprises an inlet segment coupled with the media channel inlet port, an outlet segment coupled with the media channel outlet port, and a main segment arranged between the inlet segment and the outlet segment; and
the main segment comprises a greater width than each of the inlet segment and the outlet segment.

5. The microfluidic device of claim 4, wherein the main segment contacts the fluid-permeable boundary portion of the second three-dimensional scaffold region.

6. The microfluidic device of claim 4, wherein for each microfluidic assay unit, the main segment comprises a substantially constant width.

7. The microfluidic device of claim 5, wherein for each microfluidic assay unit, the main segment comprises a semi-annular shape.

8. The microfluidic device of claim 1, wherein each microfluidic assay unit further comprises:
a plurality of first microposts arranged between the first scaffold region and the second scaffold region; and
a plurality of second microposts arranged at a boundary of the second scaffold region, and arranged between the second scaffold region and the media channel.

9. The microfluidic device of claim 1, wherein the first three-dimensional scaffold and the second three-dimensional scaffold each comprise a hydrogel.

10. The microfluidic device of claim 1, wherein for each microfluidic assay unit, the fluid-permeable interface between the media channel and the second scaffold region comprises a curved shape spanning an arc of at least 135 degrees.

11. The microfluidic device of claim 1, wherein for each microfluidic assay unit, the fluid-permeable interface between the media channel and the second scaffold region comprises a curved shape spanning an arc of at least 180 degrees.

12. The microfluidic device of claim 1, wherein for each microfluidic assay unit:
the one or more first cells comprises at least one of migratory cells, stem cells, and tumor cells; and
the one or more second cells comprises at least one of: adipocytes, fibroblasts, macrophages, T-cells, and monocytes.

13. The microfluidic device of claim 1, wherein:
each microfluidic assay unit further comprises a third scaffold region containing a third three-dimensional scaffold comprising one or more third cells, wherein the third scaffold region surrounds, and is in contact with, the fluid-permeable boundary portion of the second scaffold region; and
for each microfluidic assay unit, the third scaffold region is arranged between the second scaffold region and the media channel, wherein the fluid-permeable interface between the media channel and the second scaffold region includes a portion of the third scaffold region.

14. The microfluidic device of claim 13, further comprising:
a plurality of first microposts arranged between the first scaffold region and the second scaffold region;
a plurality of second microposts arranged between the second scaffold region and the third scaffold region; and
a plurality of third microposts arranged between the third scaffold region and the media channel.

15. The microfluidic device of claim 13, wherein for each microfluidic assay unit:
the one or more first cells comprises at least one of migratory cells, stem cells, and tumor cells;
the one or more second cells comprises at least one of adipocytes and fibroblasts; and
the one or more third cells comprises at least one of macrophages, T-cells, monocytes, vascular cells, endothelial cells, smooth muscle cells, and pericytes.

16. A method for performing an assay utilizing a microfluidic device that comprises a substrate and a plurality of microfluidic assay units arranged on the substrate, wherein each microfluidic assay unit comprises (i) a first scaffold region, (ii) a second scaffold region containing a second three-dimensional scaffold comprising one or more second cells, wherein the second scaffold region surrounds, and is in contact with, a fluid-permeable boundary portion of the first scaffold region, and (iii) a media channel surrounding a fluid-permeable boundary portion of the second scaffold region, wherein a fluid-permeable interface between the media channel and the second scaffold region comprises a curved shape spanning an arc of more than 90 degrees, the method comprising:
forming a first three-dimensional scaffold comprising a plurality of first cells in the first scaffold region;
forming a second three-dimensional scaffold comprising a plurality of second cells in the second scaffold region; and
supplying liquid media to the media channel to permit fluid communication between contents of the media channel and at least the second scaffold region.

17. The method of claim 16, further comprising, for each microfluidic assay unit, extracting liquid media from the media channel, and analyzing the extracted liquid media.

18. The method of claim 16, further comprising, for each microfluidic assay unit:
digesting at least a portion of the first three-dimensional scaffold in the first scaffold region;
removing at least some first cells of the plurality of first cells from the digested first three-dimensional scaffold of the first scaffold region; and
analyzing the at least some first cells.

19. The method of claim 16, further comprising, for each microfluidic assay unit:
digesting at least a portion of the second three-dimensional scaffold in the second scaffold region;
removing at least some second cells of the plurality of second cells from the digested second three-dimensional scaffold of the second scaffold region; and
analyzing the at least some second cells.

20. The method of claim 16, wherein:
- each microfluidic assay unit further comprises (iv) a third scaffold region that surrounds, and is in contact with, the fluid-permeable boundary portion of the second scaffold region, with the third scaffold region arranged between the second scaffold region and the media channel, and with the fluid-permeable interface between the media channel and the second scaffold region including a portion of the third scaffold region;
- the method further comprises forming a third three-dimensional scaffold comprising a plurality of third cells in the third scaffold region; and
- the supplying of liquid media to the media channel permits fluid communication between contents of the media channel and at least the second scaffold region through the third scaffold region.

21. The method of claim 20, further comprising, for each microfluidic assay unit:
- digesting at least a portion of the third three-dimensional scaffold in the third scaffold region;
- removing at least some third cells of the plurality of third cells from the digested third three-dimensional scaffold of the third scaffold region; and
- analyzing the at least some third cells.

22. The method of claim 16, further comprising performing imaging analysis of at least a portion of each microfluidic assay unit.

* * * * *